United States Patent
Jansson et al.

(10) Patent No.: US 9,623,165 B2
(45) Date of Patent: Apr. 18, 2017

(54) CASSETTE FOR PUMPING A TREATMENT SOLUTION THROUGH A DIALYZER

(71) Applicant: GAMBRO LUNDIA AB, Lund (SE)

(72) Inventors: Olof Jansson, Vellinge (SE); Sture Hobro, Lund (SE); Lennart Jonsson, Bjarred (SE); Anton Persson, Lund (SE)

(73) Assignee: Gambro Lundia AB, Lund (SE)

( * ) Notice: Subject to any disclaimer, the term of this patent is extended or adjusted under 35 U.S.C. 154(b) by 79 days.

(21) Appl. No.: 14/650,210

(22) PCT Filed: Dec. 9, 2013

(86) PCT No.: PCT/EP2013/075950
§ 371 (c)(1),
(2) Date: Jun. 5, 2015

(87) PCT Pub. No.: WO2014/090746
PCT Pub. Date: Jun. 19, 2014

(65) Prior Publication Data
US 2015/0306294 A1    Oct. 29, 2015

Related U.S. Application Data

(60) Provisional application No. 61/736,669, filed on Dec. 13, 2012.

(51) Int. Cl.
*A61M 37/00*    (2006.01)
*A61M 1/16*    (2006.01)
(Continued)

(52) U.S. Cl.
CPC ............ *A61M 1/1601* (2014.02); *A61M 1/14* (2013.01); *F17D 1/14* (2013.01); *A61M 1/165* (2014.02);
(Continued)

(58) Field of Classification Search
CPC ........ A61M 1/14; A61M 1/16; A61M 1/1601; A61M 1/1635; A61M 1/1656;
(Continued)

(56) References Cited

U.S. PATENT DOCUMENTS

2006/0196884 A1    9/2006 Gerken
2009/0012455 A1    1/2009 Childers et al.
(Continued)

FOREIGN PATENT DOCUMENTS

GB    2239904    7/1991
GB    2283065    4/1995
(Continued)

OTHER PUBLICATIONS

International Search Report—PCT/EP2013/075950—Dated Mar. 31, 2014—5 pages.
Written Opinion—PCT/EP2013/075950—Dated Mar. 31, 2014—6 pages.

*Primary Examiner* — Leslie Deak
(74) *Attorney, Agent, or Firm* — K&L Gates LLP

(57) ABSTRACT

A cassette is provided for installation in a dialysis monitor to pump a treatment solution through a dialyzer. The cassette is a unitary component with a hydraulic manifold (53) and a pneumatic manifold (54) integrated into a body (52). The body (52) has connectors for connecting the hydraulic manifold (53) to the dialyzer and the pneumatic manifold (54) to a pneumatic pressure source. A set of solution pumps is integrated in the cassette, and each solution pump includes a pump cavity inside the body. The solution pumps are operable to displace the treatment solution through the hydraulic manifold (53) to and/or from the dialyzer by action of a reciprocating gas-liquid interface in the pump cavity (30) of the respective solution pump. The gas-liquid interface is formed directly between a gaseous substance and the treatment solution. A valve arrangement (58) is attached (Continued)

to the body (52) and operable to control admission of the gaseous substance and the treatment solution to the pump cavity (30) so as to reciprocate the gas-liquid interface and thereby pump the treatment solution through the hydraulic manifold (53). The cassette is configured to pump the treatment solution without moving parts inside the body (52).

28 Claims, 12 Drawing Sheets

(51) Int. Cl.
*F17D 1/14* (2006.01)
*A61M 1/14* (2006.01)

(52) U.S. Cl.
CPC . *A61M 2205/121* (2013.01); *A61M 2205/128* (2013.01); *A61M 2205/3334* (2013.01); *A61M 2205/3375* (2013.01); *A61M 2205/3389* (2013.01); *A61M 2205/70* (2013.01)

(58) Field of Classification Search
CPC ...... A61M 2205/121; A61M 2205/128; A61M 2205/3334; A61M 2205/3375; A61M 2205/3389

See application file for complete search history.

(56) References Cited

U.S. PATENT DOCUMENTS

| | | |
|---|---|---|
| 2009/0095679 A1 | 4/2009 | Demers et al. |
| 2011/0196289 A1 | 8/2011 | Plahey et al. |
| 2012/0106289 A1 | 5/2012 | Wilt et al. |
| 2012/0259276 A1 | 10/2012 | Childers et al. |
| 2012/0261341 A1 | 10/2012 | Kreber et al. |

FOREIGN PATENT DOCUMENTS

| | | |
|---|---|---|
| WO | 9420158 | 9/1994 |
| WO | 01/17584 | 3/2001 |
| WO | 0117649 | 3/2001 |
| WO | 03/101510 | 12/2003 |
| WO | 2006120415 | 11/2006 |
| WO | 2008/106191 | 9/2008 |
| WO | 2009/094182 | 7/2009 |
| WO | 2009/094183 | 7/2009 |
| WO | 2011038858 | 4/2011 |
| WO | 2011/139234 | 11/2011 |

CASSETTE FOR PUMPING A TREATMENT SOLUTION THROUGH A DIALYZER

CROSS-REFERENCE TO RELATED APPLICATIONS

The present application is a National Phase of International Application No. PCT/EP2013/075950, filed on Dec. 9, 2013, which claims priority to Sweden Patent Application No. 1251415-4, filed Dec. 13, 2012, and U.S. Provisional Application No. 61/736,669, filed Dec. 13, 2012, the entire contents of each of which is incorporated herein by reference and relied upon.

TECHNICAL FIELD

The present invention generally relates to the field of renal replacement therapy by the use of a dialysis system for extracorporeal blood processing, and in particular to a cassette for pumping a treatment solution through a dialyzer in such a dialysis system.

BACKGROUND ART

In extracorporeal blood processing, blood is taken out of a human or animal subject, processed in a dialyzer and then reintroduced into the subject by means of an extracorporeal blood flow circuit. Such extracorporeal blood processing includes hemodialysis, hemodiafiltration, hemofiltration, ultrafiltration (fluid removal), etc.

Generally, the extracorporeal blood processing is aimed at achieving movement of water and solutes across a semipermeable membrane inside the dialyzer. In many types of extracorporeal processing, this is achieved by pumping the blood through the dialyzer on one side of the semi-permeable membrane and by pumping a treatment solution (dialysis fluid) through the dialyzer on the other side of the semi-permeable membrane.

Prior art dialysis systems comprise a complex supply arrangement for preparing and conditioning the treatment solution and for pumping the treatment solution through the dialyzer. The supply arrangement defines a fluid path which extends through a number of separate components such as pumps, valves, connectors, fluid lines, sensors, ultrafiltration measurement devices, etc. The manufacturing of such a supply arrangement is labor intensive. Also large number of connections and detachable and movable parts may lead to leakage of fluid and/or operational failure and need for maintenance.

US2012/0106289 discloses a plurality of separate cassettes that may be implemented to form functionally different parts of a supply arrangement for treatment solution in a dialysis system. A mixing cassette is implemented to mix the treatment solution and then send the treatment solution to a storing vessel or reservoir. A middle cassette is implemented to provide fluid lines and ports. A balancing cassette is implemented with balancing chambers for balancing the volume of fluid that enters the balancing cassette in one direction with the volume of fluid that enters the balancing cassette from another direction. The balancing cassette is also implemented to provide a metering function where a volume of fluid from one direction may be pumped such that it bypasses the balancing chambers and does not affect the balancing volumes. The cassettes may be combined into a cassette device/system that mixes treatment fluid, transports treatment fluid and balances the volume of treatment fluid before and after flowing through a dialyzer. Each cassette contains at least one reciprocating positive-displacement pump, denoted "pod pump". Each pod pump is formed by an essentially spherical interior cavity containing a flexible membrane that effectively divides the spherical cavity into a variable-volume pumping chamber and a complementary variable-volume actuation chamber. The actuation chamber as well as valves associated with the pod pump are pneumatically controlled. The membrane is urged to move back and forth within the cavity by alternately applying, to the actuation chamber, negative pneumatic (or atmospheric) pressure and positive pneumatic pressure. Valves at a fluid inlet and a fluid outlet of the pumping chamber are operated in synchronization with the reciprocating membrane to cause treatment fluid to be pumped through the pumping chamber. Each valve may be controlled to open and close by pneumatic pressure acting on a membrane which is installed in the cassette to cooperate with a respective valve seat. Each cassette is formed as an assembly of three plates that are formed with complementary channels to define the interior cavities of the pod pumps as well as appropriate paths for pneumatic pressure and treatment solution. To form the pod pumps and the valves, separate membranes are fitted between at least two of the plates. A similar hemodialysis system is shown in WO2008/106191.

The supply arrangements of US2012/0106289 and WO2008/106191 include several cassettes and many separate parts to be assembled in production. Thus, manufacture is complex and the supply arrangement has many points of failure as well as many connections that may cause leakage. It is realized that a failure in a moving component inside one of the cassettes results in rejection of the entire cassette, or even the entire cassette system, since it may be difficult or impossible to open the cassette to replace the failing component. Furthermore, the provision of plural membranes inside the cassette constrains the design of the cassettes and may result in an increased form factor.

In the field of peritoneal dialysis (PD), it also known to provide a disposable cassette for installation in a PD cycler for the purpose of supplying a treatment fluid. The cassette is a unitary component formed of a rigid base body or frame which defines interior cavities, and a coherent diaphragm, foil or sheeting that overlies the entire body or frame and its cavities to define pump stations, fluid paths and valve stations inside the cassette. The cassette is mounted in the cycler to interface with an actuator system which acts on the diaphragm, foil or sheeting to impart a desired movement to a treatment fluid through the cassette. The actuator system may operate to apply localized positive or negative pneumatic pressures at the diaphragm, foil or sheeting, as shown in WO94/20158, WO2009/094182, WO2009/094183 and US2009/0012455, or by operating a reciprocating piston to act on the diaphragm, foil or sheeting, as shown in US2011/0196289 and US2012/0259276.

The use of disposable cassettes for supplying blood in a blood processing apparatus is disclosed in WO01/17584, WO01/17649 and WO03/101510. These disposable cassettes also consist of a rigid base body with fitted chambers and passages and a foil or diaphragm covering them. The cassettes are mounted in a control station of the blood processing apparatus, which applies a varying pneumatic or hydraulic pressure on the foil or diaphragm to pump the blood through the cassette. The prior art also comprises so-called fluidic pumping systems in which alternating negative and positive gas pressure acts directly on a liquid in a chamber to pump the liquid through the chamber. US2006/0196884 proposes such a pumping system for bulk fluid distribution in manufacture of semiconductor devices.

GB2283065 discloses a fluidic pumping system for pumping of radioactive or hazardous liquids. Another fluidic pumping system is known from GB2239904.

Even if fluidic pumping systems are known as such, the prior art does not suggest the use of these fluidic pumping systems in medical systems in general, let alone for pumping of treatment solution in dialysis systems. Nor does the prior art suggest that these fluidic pumping systems could be integrated in cassettes or bonded manifolds. In fact, the prior art consistently teaches that cassettes for pumping a treatment solution through a dialyzer should include diaphragms, membranes or foils that are actuated to impart a desired movement to the treatment fluid through the cassette.

SUMMARY

It is an objective of the invention to at least partly overcome one or more of the above-identified limitations of the prior art.

Another objective is to achieve an improved reliability of a supply arrangement for treatment solution in a dialysis system, for example with respect to operational failure and leakage.

A further objective is to provide a supply arrangement which is suitable for mass production, for example with respect to ease of assembly and cost of assembly.

A still further objective is to enable a compact design of the supply arrangement and/or an improved flexibility in designing the supply arrangement.

One or more of these objectives, as well as further objectives that may appear from the description below, are at least partly achieved by means of a cassette, a dialysis monitor, and a method of operating a cassette according to the independent claims, embodiments thereof being defined by the dependent claims.

A first aspect of the invention is a cassette for pumping a treatment solution through a dialyzer in a dialysis system. The cassette comprises: a body a hydraulic manifold which is defined inside the body and configured for fluid communication with a first hydraulic connector on the body, the first hydraulic connector being arranged for connecting the dialyzer to the cassette a pneumatic manifold which is defined inside the body and configured for fluid communication with a first pneumatic connector on the body, the first pneumatic connector being arranged for connecting the cassette to a pneumatic pressure source a set of solution pumps integrated in the cassette and each comprising a pump cavity which is defined inside the body for fluid communication with the hydraulic and pneumatic manifolds, and a valve arrangement which is operable to selectively communicate the pump cavity with the hydraulic and pneumatic manifolds so as to, during the operation of the respective solution pump, reciprocate an interface in the pump cavity and thereby displace the treatment solution through the hydraulic manifold. The pump cavity of the respective solution pump defines, during operation of the solution pump, the interface as a direct gas-to-liquid interface in the pump cavity between a gaseous substance admitted via the pneumatic manifold and the treatment solution admitted via the hydraulic manifold.

By designing the solution pump to be driven by gas movement through a direct gas-to-liquid interface ("gas-liquid interface") inside the pump cavity, the pumping of the treatment solution is achieved without the need for installing moving parts, such as a membrane, diaphragm, piston or plunger, in the cassette. The integration of a set of membrane-free solution pumps in the cassette will facilitate manufacture of the cassette and will also reduce the likelihood for leakage and operational failure. Furthermore, the inventive use of a gas-liquid interface for pumping treatment solution through the cassette also provides greater freedom of design, e.g. with respect to the placement of the set of solution pumps in the cassette, since the solution pump(s) need not be placed to allow for mounting of membranes or other moving parts during manufacture of the cassette. The improved freedom of design may also enable a more compact design of the cassette.

The set of solution pumps may consist of a single solution pump or plural solution pumps, depending on implementation. Each solution pump defines an integrated, volumetric, positive displacement pump, which operates in a repeating cycle of a filling phase, in which a given volume of liquid is drawn into the pump cavity through one or more inlets by movement of the gas-liquid interface, and a pumping or emptying phase, in which the given volume of liquid is pushed out of the pump cavity through one or more outlets by movement of the gas-liquid interface. The individual solution pump thereby produces a pulsating or intermittent output flow. In order to achieve a continuous or semi-continuous output flow, two or more solution pumps may be connected in parallel, and the valve arrangement may be operable to drive the gas-liquid interface in mutually time-shifted phases in the pump cavities of the parallel solution pumps such that the output flow and/or input flow of the pump cavities is essentially continuous.

The hydraulic manifold is a system of channels or tracks that distribute liquid inside the body of the cassette. The hydraulic manifold typically defines internal fluid paths that extend from openings or ports, which are defined on the exterior of the body, to cavities (e.g. pump cavities), which are defined inside the body. The hydraulic manifold may also define internal fluid paths that extend between such cavities inside the body. The hydraulic manifold may be used for distributing a single liquid, the treatment solution, inside the cassette. In other embodiments, the hydraulic manifold may be designed to distribute more than one liquid, e.g. different liquid constituents that are mixed inside the cassette to form the treatment solution (see below).

The pneumatic manifold is a system of channels or tracks that distribute gas pressure inside the body of the cassette. The pneumatic manifold typically defines internal fluid paths that extend from openings or ports, which are defined on the exterior of the body to cavities (e.g. pump cavities), which are defined inside the body. The pneumatic manifold may also define internal fluid paths that may extend between such cavities inside the body.

The pump cavity of the respective solution pump defines one or more inlets and one or more outlets at the lower portion of the pump cavity, which inlet(s) and outlet(s) are connected to the hydraulic manifold. The above-mentioned valve arrangement may be further configured to allow fluid communication through the inlet(s) and prevent fluid communication through the outlet(s) during the filling phase, and prevent fluid communication through the inlet(s) and allow fluid communication through the outlet(s) during the emptying phase. This synchronized operation of the valve arrangement may be achieved by one-way valves (also known as check valves or non-return valves) that are arranged upstream of the inlet(s) and downstream of the outlet(s) to control the liquid flow. The one-way valves are thus driven to automatically open and close by the hydraulic pressure differential across the respective one-way valve. Alternatively, the valve arrangement comprises actively controlled valves which are arranged upstream of the inlet(s)

and downstream of the outlet(s) and which are actively controlled to open and close in synchronization with the filling and emptying phases. The use of active control may provide better control of the opening and closing of the inlet and outlet valves, and may also enable additional functionality, e.g. gas removal, leakage testing, changing the opening and closing times in relation to filling and emptying phases, etc. The valve arrangement may be electrically, pneumatically or hydraulically controlled.

The reciprocating motion of the gas-liquid interface, and thus the operation of the solution pump, is driven by the switching of the valve arrangement to selectively communicate an upper portion of the pump cavity with one or more pneumatic pressure sources. A single pneumatic pressure source may e.g. be used if the backing pressure of the liquid at the inlet(s) of the pump cavity is sufficiently high to drive the liquid into the pump cavity during the filling phase while the pump cavity is vented to ambient via the pneumatic manifold. In such an embodiment, the pneumatic pressure source may be configured to generate a positive gas pressure which is sufficient to push the liquid out of the pump cavity during the emptying phase.

In another embodiment, the first pneumatic connector is arranged for connecting the cassette to a pneumatic positive pressure source, and the pneumatic manifold is further in fluid communication with a second pneumatic connector on the body for connecting the cassette to a pneumatic negative pressure source, and the valve arrangement is operable to alternately communicate the pump cavity with the pneumatic positive pressure source and the negative pneumatic pressure source so as to reciprocate the gas-liquid interface in the pump cavity. A "positive" and "negative" pressure source is intended to indicate a pressure source that generates a pressure that is greater and smaller, respectively, than the backing pressure of the liquid in the hydraulic manifold. The combination of a positive pressure source and a negative pressure source allows the reciprocating motion of the gas-liquid interface to be more accurately and/or reliably controlled.

The volumetric flow rate (output flow rate) out of the individual solution pump may, e.g., be varied by controlling, via the valve arrangement, at least one of the stroke lengths of the reciprocating gas-liquid interface in the pump cavity and the frequency of the filling and emptying phases. The stroke length may be set or controlled based on the output of one or more level detectors associated with the pump cavity. The level detector(s) may be of any conventional type that allows single-point, multi-point or continuous level detection, such as an ultrasonic detector, an optical detector, a capacitive detector, a microwave sensor, etc.

In one embodiment, each solution pump is associated with an ultrasound transceiver arranged at one end of the pump cavity, and the pump cavity has a one or more reflection surfaces at known distances to the ultrasound transceiver. This type of level detector enables a continuous level detection at high accuracy. The reflection surface(s) result in well-defined echoe(s) in the output signal of the ultrasound transceiver and may be used for inherent calibration of the output signal to achieve a highly accurate level measurement. The pump cavity may be provided with more than two reflection surfaces to improve the accuracy further.

In a specific embodiment, the pump cavity has a reflection surface at a predetermined distance to the ultrasound transceiver, and a controller is connected to the ultrasound transceiver and operable to: identify a reference travelling time for a sound wave emitted by the ultrasound transceiver and reflected back to the ultrasound transceiver by the reflection surface, identify a current travelling time for a sound wave emitted by the ultrasound transceiver and reflected back to the ultrasound transceiver by the gas-liquid interface, and determine a location of the gas-liquid interface in the pump cavity as a function of the current travelling time, the reference travelling time and the predetermined distance.

In another specific embodiment, the pump cavity has at least two reflection surfaces at different predetermined distances from the ultrasound transceiver, and a controller is connected to the ultrasound transceiver and operable to: identify a respective reference travelling time for a sound wave emitted by the ultrasound transceiver and reflected back to the ultrasound transceiver by the at least two reflection surfaces, calculate an average speed of sound in the treatment solution inside the pump cavity based on the respective reference travelling times and the different predetermined distances, identify a current travelling time for a sound wave emitted by the ultrasound transceiver and reflected back to the ultrasound transceiver by the gas-liquid interface; and determine a location of the gas-liquid interface in the pump cavity as a function of the current travelling time and the average speed of sound.

In another specific embodiment, the pump cavity has at least two reflection surfaces at different predetermined distances from the ultrasound transceiver, and a controller is connected to the ultrasound transceiver and operable to: identify a respective reference travelling time for a sound wave emitted by the ultrasound transceiver and reflected back to the ultrasound transceiver by the at least two reflection surfaces, identify a current travelling time for a sound wave emitted by the ultrasound transceiver and reflected back to the ultrasound transceiver by the gas-liquid interface, and determine a location of the gas-liquid interface in the pump cavity by interpolation among the different predetermined distances based on the relation of the current travelling time to the respective reference travelling time.

Corresponding embodiments for level detection, using an ultrasound transceiver in combination with one or more reflection surfaces, may be implemented in the calibration cavity of the calibration subsystem (see below).

It should be understood that the set of solution pumps may be combined with conventional positive displacement pumps that may also be attached to or integrated in the body in fluid communication with the hydraulic manifold. Such conventional pumps include gear pumps, piston pumps, membrane pumps, etc.

The cassette may be implemented as a unitary device with one or more hydraulic connectors and one or more pneumatic connectors. The body of the cassette may also comprise dedicated structures for mounting of additional equipment in operative engagement with the hydraulic manifold and the pneumatic manifold, such as pressure sensors, blood detectors, etc. The body may be made of plastic material or metal.

In one embodiment, the body defines a plurality of valve ports on an external surface on the body, each of the valve ports being arranged in fluid communication with either the hydraulic manifold or the pneumatic manifold, wherein the valve arrangement comprises a plurality of valves that are attached to the external surface of the body in operative engagement with the valve ports, the valves being operable to selectively communicate the pump cavity of the respective solution pump with the hydraulic and pneumatic manifolds by the operative engagement with the valve ports. This results in a compact design of the cassette. Further, maintenance and repair is facilitated, since it is simple to replace the valves and inspect the valve ports. The plurality of valves may be electrically controlled.

By this design, with valves attached to the external surface of the body, the cassette is suitable for permanent installation in a dialysis machine, or at least for use in a plurality of treatment sessions (semipermanent), since the valves are accessible for maintenance and repair. The valves, which contain moving parts, may be the most likely point of failure during operation of the cassette for a prolonged period of time. Thus, the cassette of this embodiment is not designed as a disposable to be discarded after each treatment session but as a reusable component for permanent or semipermanent installation in a dialysis machine.

In one embodiment, the hydraulic manifold comprises a dedicated fluid path in the region of the valve ports, the dedicated fluid path being configured to convey at least part of heat emitted by the plurality of valves to the treatment solution before the treatment solution is provided to the dialyzer. Thereby, the hydraulic manifold implements a heat exchanger for cooling of the valves, by removing heat that may be accumulated around the valves, especially if the body is made of plastic material. The heat exchanger enables a reduced power consumption of the dialysis system since part of the heat is used for pre-heating of the treatment solution as such and/or for pre-heating of one or more of the liquid constituents that form the treatment solution by mixing inside the body (see below).

In one embodiment, the body comprises a plurality of solid plates of plastic material that collectively define the hydraulic manifold, the pneumatic manifold and the pump cavities (and the metering and calibration cavities, if present) and which are assembled to form a rectangular cuboid. The use of solid plates may facilitate manufacture of the manifolds and cavities inside the body. The combination of solid plates may also enable a more compact design of the cassette, since the manifolds and cavities may extend in plural layers in the body. For example, the manifolds and cavities may be created in one or more of the solid plates by machine processing, injection molding, etc. The use of plastic material enables low weight and provides the option of forming the body in transparent material, to allow visual inspection of the manifolds and cavities, e.g. with respect to clogging and other obstructions or malfunctions that may occur during use.

In one embodiment, the solid plates are assembled by diffusion bonding. Diffusion bonding allows the solid plates to be permanently joined without the use of solvents or adhesives, which might otherwise form obstructions in the manifolds and cavities when the plates have been assembled. The absence of solvents and adhesives also reduces the risk for contamination of the manifolds and cavities, which may be an attractive property in a cassette for handling medical fluids. Diffusion bonding results in strong joints. In alternative embodiments, the solid plates are permanently joined by another technique for joining plastic materials, such as High Accuracy Bond (HAB®) techniques, plastic cementing, adhesive bonding, ultrasonic welding, etc.

In one embodiment, one pair of the solid plates is configured to collectively define at least one of the hydraulic manifold and the pneumatic manifold, and another pair of the solid plates are configured to collectively define all cavities. Such a physical separation of at least one of the manifolds from the cavities may enable a better optimization of the manifolds and the cavities, e.g. with respect to manifold diameter, manifold extent, cavity placement, etc. Furthermore, by defining the manifold(s) and the cavities by pairs of plates, manufacturing may be facilitated. For example, the manifold(s) and the cavities may be formed as mating recesses in the faces of the plates.

In another embodiment, all cavities are defined in one of the solid plates. Such an embodiment may enable use of a reduced number of plates in the body and thus a reduced thickness of the cassette.

The cassette may be implemented to pump the treatment solution to a dialyzer. In one such embodiment, the cassette comprises an upstream subsystem for pumping the treatment solution to the dialyzer, and the set of solution pumps comprises at least one solution pump in the upstream subsystem, referred to as "upstream solution pump" in the following.

Alternatively, the cassette may be implemented to pump the treatment solution from the dialyzer. In one such embodiment, the cassette comprises a downstream subsystem for pumping the treatment solution from the dialyzer, and the set of solution pumps comprises at least one solution pump in the downstream subsystem, referred to as "downstream solution pump" in the following.

In yet another alternative, the cassette may be implemented to pump the treatment solution both to and from the dialyzer, i.e. the treatment solution is both pumped into the dialyzer at an inlet end and pumped out of the dialyzer at an outlet end. In one such embodiment, the cassette comprises an upstream subsystem for providing the treatment solution to the dialyzer via the first hydraulic connector, and a downstream subsystem for pumping the treatment solution from the dialyzer via a second hydraulic connector, wherein the set of solution pumps comprises an upstream solution pump in the upstream subsystem and a downstream solution pump in the downstream subsystem. By connecting the cassette with its upstream and downstream pumps in series over the dialyzer, the cassette may be arranged to control the flow of treatment solution through the dialyzer, e.g. as part of a system for controlling ultrafiltration (UF) in the dialyzer.

In one embodiment, the valve arrangement is operable to balance the volumetric flow rates of the upstream and downstream solution pumps, i.e. the output flow rate of the upstream solution pump and the input flow rate of the downstream solution pump. To achieve ultrafiltration, the hydraulic manifold may include an additional fluid path connected to a dedicated ultrafiltration pump. The additional fluid path may extend from a fluid path between the dialyzer and the downstream solution pump, to a drain for treatment solution. The volumetric pumping rate of the ultrafiltration pump thereby controls the ultrafiltration in the dialyzer. The ultrafiltration pump may be incorporated in the cassette, e.g. configured as a solution pump.

In another embodiment, which obviates the need for a dedicated ultrafiltration pump, the valve arrangement is operable to set a difference in volumetric flow rates between the upstream and downstream solution pumps so as to control ultrafiltration in the dialyzer. Thus, ultrafiltration is given by the excess in volumetric flow rate between the downstream and upstream solution pumps, i.e. the volumetric difference between the input flow rate of the downstream solution pump and the output flow rate of the upstream solution pump.

Irrespective of application, it may be necessary to relatively calibrate the volumetric flow rates of the upstream and downstream solution pumps, e.g. to account for differences caused by manufacturing tolerances, deposits, systematic errors and drifts in level detectors, drifts in the timing of the valve arrangement, etc. In one such embodiment, the cassette further comprises a calibration subsystem for relatively calibrating the upstream solution pump and the downstream solution pump, wherein the calibration subsystem comprises a calibration cavity which is defined inside the body and connected for fluid communication with a bypass line that extends between the upstream and downstream solution pumps, wherein level detectors are associated with the upstream and downstream solution pumps to indicate levels of the treatment solution in the respective pump cavity, wherein the cassette is operable to reciprocate the gas-liquid interface between an upper level and a lower level in the respective pump cavity so as to pump the treatment solution between the upstream and downstream solution pumps through the bypass line, and wherein the valve arrangement is operable to selectively control the fluid communication between the bypass line and the calibration cavity. This embodiment offers a simple, compact and robust calibration subsystem which is integrated in the cassette. This embodiment further allows the cassette to be operated in a calibration phase, in which the valve arrangement is operable to: cause one of the upstream and downstream solution pumps to perform an emptying stroke that moves the gas-liquid interface from an upper reference level to a lower reference level so as to push the treatment solution into the bypass line; cause the other of the upstream and downstream solution pumps to perform a filling stroke that moves the gas-liquid interface from the lower reference level to the upper reference level so as to draw the treatment solution from the bypass line; and selectively establish fluid communication between the bypass line and the calibration cavity during the emptying and filling strokes so as to transfer a known or measurable calibration volume between the calibration cavity and the pump cavity of the upstream solution pump or the downstream solution pump, wherein one of the level detectors is operable to measure a level change corresponding to the calibration volume in said pump cavity of the upstream solution pump or the downstream solution pump.

The calibration phase is designed based on the insight that a robust and simple calibration of the solution pumps can be achieved by quantifying the level change in one of the pump cavities when a well-defined volume of treatment solution enters or leaves the pump cavity.

One general advantage of the calibration subsystem is that it relaxes the tolerance requirements of the solution pumps. If the cassette includes more than one upstream or downstream solution pump, all of the upstream and downstream pumps may be relatively calibrated in pairs by use of a single calibration cavity.

In one embodiment, the cassette further comprises, or is connected to, a controller which is coupled to the level detectors and configured to: determine, during the calibration phase, a balancing level in said pump cavity of the upstream solution pump or the downstream solution pump, such that the filling and emptying strokes have equal volumes when the balancing level replaces the lower or upper reference level in said pump cavity; and determine an adjusted stroke length for the direct gas-to-liquid interface in said pump cavity of the upstream solution pump or the downstream solution pump as a function of the measured level change, the determined balancing level, and the known or measurable calibration volume, so as to achieve a given volumetric difference between the upstream and downstream solution pumps.

The balancing level may be determined in any conceivable way, which may or may not involve the calibration cavity. For example, one of the solution pumps may be operated to move the gas-liquid interface in a filling stroke or emptying stroke between the lower and upper reference levels, while the other solution pump is operated to move the gas-liquid interface in an emptying or filling stroke from the upper reference level and lower reference level, respectively. Provided that all of the displaced treatment solution is transferred between the solution pumps, the balancing level is given as the final level of the gas-liquid interface in the other solution pump.

In one embodiment, the controller is configured to determine the adjusted stroke length by setting one of the lower and upper levels in the upstream solution pump or the downstream solution pump at a distance $\Delta h_{UF}$ from the determined balancing level, $\Delta h_{UF} = V_{UF}/V_{CAL} \cdot \Delta h$, wherein $V_{UF}$ is the given volumetric difference, $V_{CAL}$ is the known or measurable calibration volume, and $\Delta h$ is the measured level change.

In one implementation, the cassette comprises a further level detector operable to indicate levels of treatment solution in the calibration cavity, wherein the valve arrangement, in the calibration phase, is operable to: selectively establish fluid communication between the bypass line and the calibration cavity during the emptying and filling strokes so as to change an initial level of treatment solution in the calibration cavity in proportion to a volumetric difference between the emptying and filling strokes, said volumetric difference being the calibration volume and being measurable by the further level detector. Thus, the volumetric difference between the upstream and downstream solution pumps is represented by a level difference which is detected by the level detector in the calibration cavity and converted into volume. The initial level in the calibration cavity may, but need not, be predefined but should be selected so as to allow for detection of both an increased and a decreased level difference.

In one embodiment, the valve arrangement is operable, in the calibration phase, to perform the emptying and filling strokes in synchronization, i.e. such that the emptying and filling strokes are initiated concurrently. Furthermore, the valve arrangement may be operable, in the calibration phase, to selectively establish the fluid communication between the bypass line and the calibration cavity only when the level detectors associated with the pump cavities indicate that the emptying stroke has reached the lower reference level or that the filling stroke has reached the upper reference level. This means that only a volume of treatment solution corresponding to the volumetric difference will enter or leave the calibration cavity during the calibration phase, and thus that the calibration cavity may be small and compact. Furthermore, this embodiment ensures that the initial level of treatment solution in the calibration cavity is changed in proportion to the volumetric difference between the emptying and filling strokes.

It is to be understood that the filling and emptying strokes may be repeated during the calibration phase, such that level difference in the calibration cavity represents an accumulated volumetric difference for all emptying and filling strokes during the calibration phase. This may improve the accuracy of the calibration volume and the corresponding level change.

In an alternative implementation, the cassette comprises a further level detector operable to indicate levels of treatment solution in the calibration cavity, wherein the valve arrangement, in the calibration phase, is operable to: selectively establish fluid communication between the bypass line and the calibration cavity during the emptying and filling strokes, so as to push the treatment solution into the calibration cavity to increase a level of treatment solution in the calibration cavity from an initial level to a final level, as indicated by the further level detector, and to draw the treatment solution from the calibration cavity to decrease the level of treatment solution in the calibration cavity from the final level to the initial level, wherein the calibration cavity is configured to contain the calibration volume between the initial and final levels. Thus, in this implementation, the calibration volume is known.

Generally, any type of level detector may be used to detect and measure the level difference in the calibration cavity, e.g. the level detectors mentioned above in relation the solution pumps.

In one embodiment, the emptying stroke is performed by the upstream solution pump during the calibration phase (and the filling stroke is thus performed by the downstream solution pump). This may reduce the risk for accumulation of deposits in the calibration subsystem since it receives fresh treatment solution via the bypass line, i.e. treatment solution that has not passed the dialyzer.

The cassette may be arranged to receive and pump a pre-mixed (ready-made) treatment solution.

In an alternative, the cassette may be configured to prepare the treatment solution by mixing at least two liquid constituents, which may be obtained from reservoirs or supplies external to the cassette. The liquid constituents may comprise water and one or more concentrates. For example, it is known in the art to generate a treatment solution by mixing water with a base concentrate containing sodium bicarbonate (also known as "B concentrate") and an acid concentrate (also known as "A concentrate").

In one embodiment, the upstream subsystem is further configured to prepare the treatment solution by mixing at least two liquid constituents, and the pump cavity of the upstream solution pump has at least one inlet connected to receive the liquid constituents from the hydraulic manifold, whereby motion of the gas-liquid interface in the pump cavity causes the liquid constituents to enter via the at least one inlet and mix in the pump cavity to form the treatment solution. This provides space-efficient mixing, since the motion of the gas-liquid interface is at least partially used for the mixing. In one implementation, the hydraulic manifold is configured to allow at least some of the liquid constituents to meet upstream of the upstream pump, such that they are partially mixed before they enter the pump cavity, where they then are mixed further. In another implementation, the hydraulic manifold is configured to convey the liquid concentrates on separate fluid paths to the solution pump, such that mixing takes place in the pump cavity only. It should be noted that these implementations may be combined, such that certain portions of the liquid constituents are partially mixed in the hydraulic manifold, while other portions enter the pump cavity on separate fluid path(s) to mix in the pump cavity only.

The concentrates may be drawn into the hydraulic manifold only by the action of the gas-liquid interface in the upstream solution pump. However, to achieve a higher accuracy in the dosing of the concentrates, one or more dedicated concentrate pumps may be attached to or integrated in the cassette to pump a metered dose of the respective concentrate into the hydraulic manifold. Any conventional pump may be used as concentrate pump, such as gear pumps, piston pumps, membrane pumps, etc. However, a space-efficient, simple, accurate and robust metering of concentrate is achieved by using the same design for the concentrate pump(s) as for the solution pump(s). In one such embodiment, the concentrate pump comprises a metering cavity which is defined inside the body and connected to the hydraulic and pneumatic manifolds for defining a direct gas-to-concentrate interface in the metering cavity, wherein the valve arrangement is operable to selectively communicate the metering cavity with the pneumatic manifold so as to, during operation of the concentrate pump, reciprocate the direct gas-to-concentrate interface in the metering cavity and thereby draw concentrate from the hydraulic manifold through a concentrate inlet into the metering cavity and displace the concentrate from the metering cavity through a concentrate outlet into the hydraulic manifold, wherein the concentrate outlet is arranged for fluid communication with the upstream solution pump.

It may be important to remove gases from the treatment solution, to ensure proper operation of the solution pumps and the dialyzer. One significant advantage of the inventive use of solution pumps with a gas-liquid interface is that gases, e.g. air, that may be entrapped or dissolved in the liquid that enters the pump cavity will at least partly be removed from the liquid during the filling phase when the pump cavity is communicated with the pneumatic manifold to lower the pneumatic pressure in the pump cavity. Thereby, the solution pump has an inherent gas removal function. In one embodiment, which may achieve a more consistent and efficient gas removal, the valve arrangement is operable, in a gas removal phase during operation of the cassette, to seal off the pump cavity from the hydraulic manifold and selectively communicate the pump cavity with the pneumatic manifold to establish a negative pressure in the pump cavity.

A second aspect of the invention is a dialysis monitor, comprising the cassette of the first aspect as set forth above and a controller for controlling the operation of the valve arrangement. The second aspect shares the advantages of the first aspect.

The invention also generally relates to a method of operating the cassette according to the first aspect, by performing steps for controlling the operation of the valve arrangement and, as applicable, for retrieving readings from the level detectors and for computing settings for the operation of the valve arrangement, e.g. based on the above-described calibration phase. For example, such a method for operating the cassette in the calibration phase may comprise the steps of: determining, during the calibration phase, a balancing level in said pump cavity of the upstream solution pump or the downstream solution pump, such that the filling and emptying strokes have equal volumes when the balancing level replaces the lower or upper reference level in said pump cavity; and determining an adjusted stroke length for the direct gas-to-liquid interface in said pump cavity of the upstream solution pump or the downstream solution pump as a function of the level change, the balancing level, and the calibration volume, so as to achieve a given volumetric difference between the upstream and downstream solution pumps.

Still other objectives, features, aspects and advantages of the present invention will appear from the following detailed description, from the attached claims as well as from the drawings.

BRIEF DESCRIPTION OF DRAWINGS

Embodiments of the invention will now be described in more detail with reference to the accompanying schematic drawings.

DETAILED DESCRIPTION OF EXAMPLE EMBODIMENTS

Figure 1:
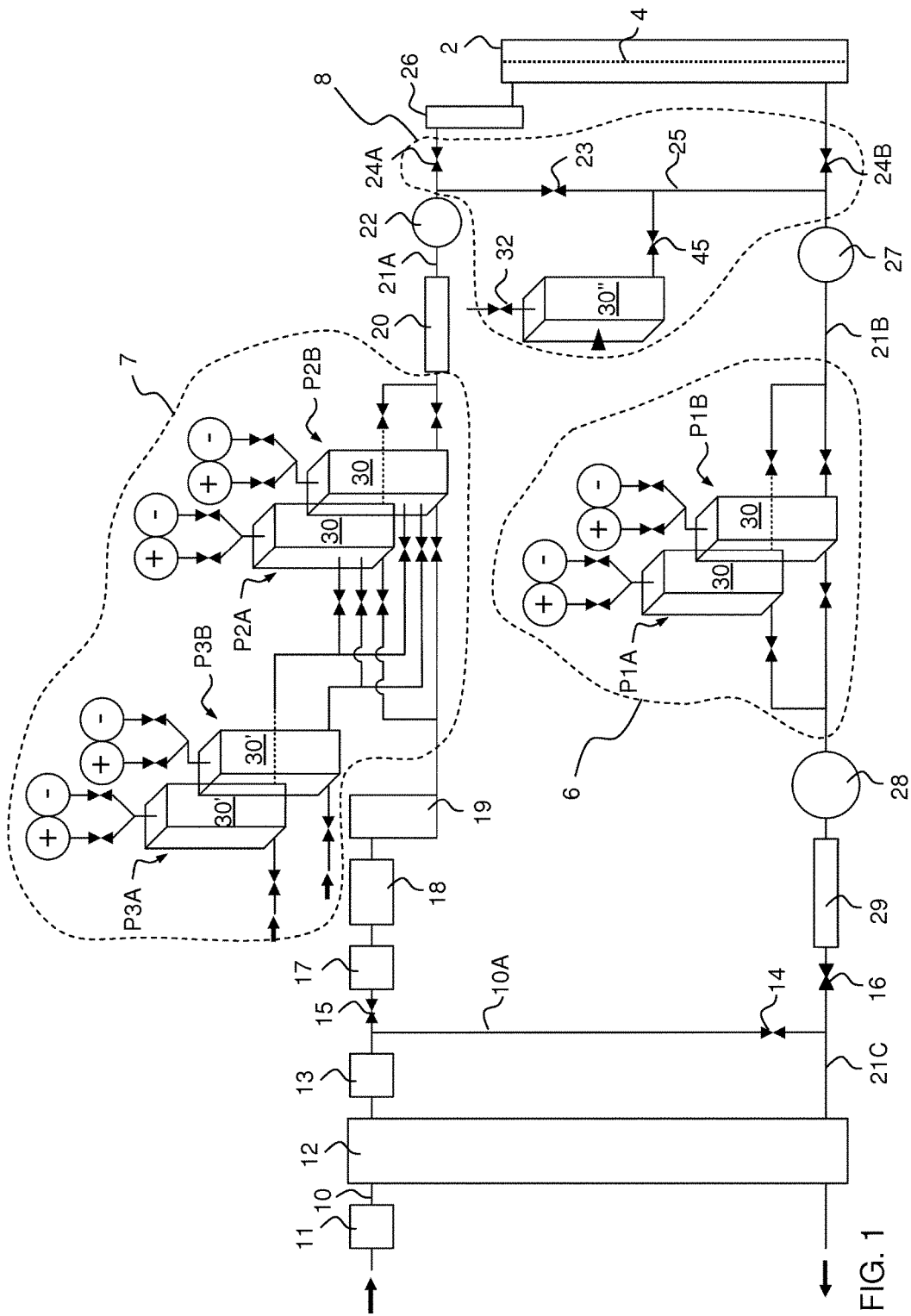
FIG. 1 is a fluid flow-path schematic of a supply arrangement for treatment solution according to an embodiment.

Exemplary embodiments of the present invention will now be described with reference to integrated supply arrangements for providing a treatment solution in a dialysis system. Throughout the description, the same reference numerals are used to identify corresponding elements.

FIG. 1 is a fluid-flow diagram of a supply arrangement according to an embodiment of the invention. The supply arrangement is part of a dialysis machine and defines a flow path for a treatment solution (dialysis fluid) through a dialyzer 2. The dialyzer 2 is a conventional blood treatment device suitable for solute removal as well as ultrafiltration, such as a coil dialyzer, a parallel plate dialyzer, a hollow fiber dialyzer, etc. The dialyzer 2 generally has a blood side and a fluid side separated by a semipermeable membrane 4. In operation of the dialysis machine, an extracorporeal blood flow circuit (not shown) is connected to the blood side of the dialyzer 2 and arranged to circulate blood from a patient through the dialyzer 2 and back to the patient. Concurrently, the supply arrangement is operated to pump the treatment solution on the fluid side of the dialyzer 2 whereby solutes are transported over the membrane 4 due to a concentration gradient and/or ultrafiltrate is transported over the membrane due to a pressure gradient. Any resulting ultrafiltrate contains excess water and possibly also solutes from the blood.

The supply arrangement is operable to prepare the treatment solution with a suitable composition, pressure and temperature and pump it to an inlet on the fluid side of the dialyzer 2. The supply arrangement is also operable to pump the treatment fluid from an outlet on the fluid side of the dialyzer 2 to a drain. In the illustrated embodiment, the supply arrangement includes three sub-systems 6-8 that are implemented by a single unitary cassette. A downstream pump sub-system 6 (also denoted "downstream module") is configured to pump the treatment solution from the dialyzer 2. An upstream pump sub-system 7 (also denoted "upstream module") is configured to prepare the treatment solution by mixing water with concentrates, and to pump the resulting treatment solution to the dialyzer 2. A calibration sub-system 8 (also denoted "taration module") is configured to relatively calibrate the volumetric flow rates of the downstream and upstream modules 6, 7.

The following description focuses on the design of the sub-systems 6-8 and their integration in the cassette. Therefore, only a brief explanation is given below about the operation of the supply arrangement as a whole. Components that do not form part of the cassette are only briefly described. Although not shown in FIG. 1, the operation of the supply arrangement is controlled by a control system (controller) which retrieves measurement signals from various detectors/sensors and generates control signals for valves to selectively open and close fluid paths in the supply arrangement. It should be emphasized that the illustrated configuration of the supply arrangement is merely given as an example.

The supply arrangement includes a water supply line 10 which is connected to receive water from a water purification system (not shown). The water supply line 10 includes a pressure reducer 11 that lowers the pressure of the incoming water before the water is directed through a heat exchanger 12. The heat exchanger 12 is arranged to raise the temperature of the incoming water by heat exchange with the treatment solution that is pumped out of the dialyzer 2 by the downstream module 6. A pressure sensor 13 is arranged in the water supply line 10 downstream of the heat exchanger 12. If the pressure sensor 13 indicates that the water pressure is too high, a bypass valve 14 is opened and system valves 15, 16 are closed, such that the incoming water is directed via a first bypass line 10A to the drain (not shown). If the water pressure is correct, the water is led through another pressure reducer 17 and a flow switch 18. A heater 19 is arranged to heat the water to a pre-set temperature, e.g. body temperature. The water then enters the upstream module 7. A conductivity cell 20 is arranged in a first solution path 21A after the module 7 to monitor the composition of the treatment solution, and a pressure sensor 22 is arranged to monitor the pressure of the treatment solution. If the composition and/or pressure is wrong, an intermediate bypass valve 23 is opened and intermediate system valves 24A, 24B are closed, such that the treatment solution is directed via a second bypass line 25 directly to the downstream module 6. In the illustrated embodiment, at least the second bypass line 25 and the valves 23, 24A, 24B form part of the taration module 8 in the cassette. If the properties of the treatment solution are correct, the treatment solution is led through a fluid filter 26 to the dialyzer 2. A pressure sensor 27 is arranged in a second solution path 21B between the dialyzer outlet and the downstream module 6 to monitor the pressure of the treatment solution, and a blood leak detector 28 is arranged in a third solution path 21C after the downstream module 6 to check the treatment solution for blood. If blood is found to leak into the supply arrangement, the dialysis machine is shut down and an alarm is issued. A conductivity cell 29 is arranged after the blood leak detector 28 to monitor the composition of the treatment solution before the treatment solution is directed via the system valve 16 and the heat exchanger 12 to a drain.

The supply arrangement is operated to achieve a given amount of ultrafiltration during a treatment session. The ultrafiltration (UF) rate during the treatment session is governed by the difference in volumetric flow rate of treatment solution out of and into the dialyzer 2. As used herein, the volumetric flow rate refers to an average flow rate during a few pumping cycles for the pumps in the downstream and upstream modules 6, 7. Thus, the supply arrangement is controlled to generate a volumetric flow of treatment fluid to and from the fluid side dialyzer 2 so as to produce a UF rate that follows a predetermined track during the treatment session. It should be noted that the instantaneous UF rate, e.g. during a single pumping cycle, may deviate from the track. For example, a certain backfiltration may be allowed.

In the embodiment of FIG. 1, the difference in volumetric flow rate is generated by the downstream module 6 being operated to generate a higher volumetric flow rate than the upstream module 7. The UF rate may in principle be varied by changing the pumping rate of either the downstream module 6 or the upstream module 7, or both. However, it may be more complicated to modify the pumping rate of the upstream module 7, while ensuring a consistent composition of the treatment fluid, since the upstream module 7 is configured to also prepare the treatment fluid.

In an alternative embodiment, not shown, the downstream and upstream modules 6, 7 are balanced to generate the same volumetric flow rate. Such an embodiment may require the downstream and upstream modules 6, 7 to operate in synchronization. The ultrafiltration is controlled by an additional flow rate of treatment fluid generated by a dedicated ultrafiltration pump, which is arranged to pump treatment fluid from the dialyzer 2 to the drain through a separate fluid line connected to the second solution path 21B.

Figure 2:
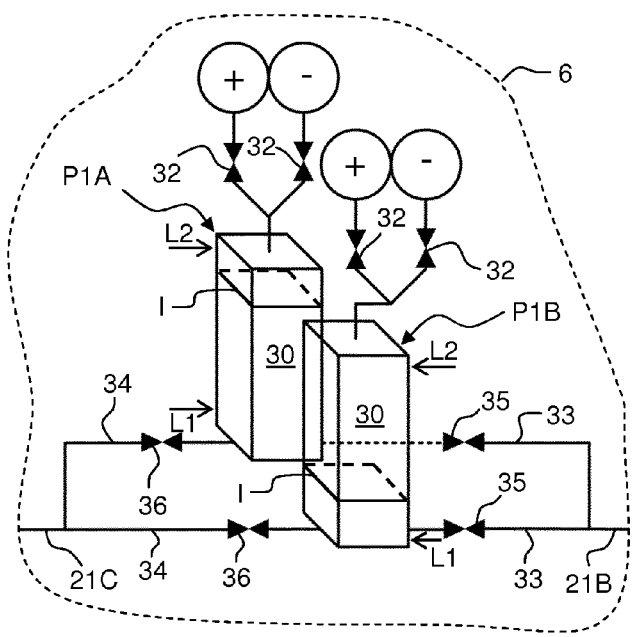
FIG. 2 is a fluid flow-path schematic of a downstream subsystem in the supply arrangement of FIG. 1.

FIG. 2 illustrates an embodiment of the downstream module 6 in FIG. 1. The downstream module includes two solution pumps P1A, P1B that are connected in parallel. Each solution pump P1A, P1B is designed to define a pump cavity 30 a direct interface I between a motive gas and the liquid to be pumped through the pump cavity 30. The cavity 30 is connected to a positive pressure source and a negative pressure source via an air port at the top portion of the cavity 30. In the drawings, the positive and negative pressure sources are schematically indicated by encircled+ and −, respectively. Valves 32 for air control are arranged between the air ports and the pressure sources and are operable to open and close a fluid path between the cavity 30 and the respective source. In one embodiment (not shown), hydrophobic membranes are arranged in the air ports or in the fluid paths between the air ports and the sources, to ensure that the pressure sources are not contaminated by liquid from the cavity. A liquid inlet and a liquid outlet are provided at the bottom portion of the cavity 30 in fluid communication with an inlet line 33 and an outlet line 34, respectively. Valves 35, 36 for liquid control are arranged in the inlet and outlet lines 33, 34 and are operable to open and close the respective inlet and outlet line 33, 34. The valves 32 for air control are controlled to alternately establish a positive and a negative pressure of motive gas in the upper portion of the cavity 30. When a negative pressure of motive gas is established, the inlet valve 35 is opened and the outlet valve 36 is closed to draw treatment solution into the cavity 30 via the liquid inlet. When a positive pressure of motive gas is established, the inlet valve 35 is closed and the outlet valve 36 is opened to push the treatment solution out of the liquid outlet. Thereby, the treatment solution is pumped through the cavity 30 by the action of a reciprocating gas-liquid interface I in the cavity 30. In a filling phase, the gas-liquid interface I is thus driven from a lower level L1 to an upper level L2 in the cavity 30. In an emptying phase, the gas-liquid interface I is driven from the upper level L2 back to the lower level L1. The volume between the lower and upper levels L1, L2 defines the stroke volume of the solution pump P1A, P1B. Since each solution pump P1A, P1B operates in alternating filling and emptying phases, a pulsating flow of treatment solution is generated through the outlet line 34.

In the illustrated embodiment, the parallel pumps P1A, P1B are operated in opposite phases, such that one pump is in the filling phase while the other is in the emptying phase, and vice versa. A continuous or almost continuous flow of treatment solution into, and possibly also out of, the downstream module 6 may be achieved by controlling the switching of the air valves 32. Optionally, the momentary flow rate into and/or out of the pump P1A, P1B may be adjusted by adjustable valves or flow restrictors (not shown) in the inlet and/or outlet lines 33, 34. For example, such valves/restrictors may be adjusted to provide an essentially constant flow rate of treatment solution during the entire filling and emptying phases.

The input flow rate of the downstream module 6 may be set by modifying the stroke volume of one or both pumps P1A, P1B while operating the pumps P1A, P1B at a fixed switching frequency between the emptying and filling phases. The stroke volume is changed by modifying the location of the lower and/or upper level L1, L2 in the pump cavity 30. Alternatively, the input flow rate may be set by modifying the switching frequency while operating the pumps P1A, P1B at fixed stroke volumes. A combination of controlling the switching frequency and the stroke volume is conceivable. Both the stroke volume and the switching frequency may be controlled by the timing of the opening and closing of the air valves 32, and possibly by corresponding control of the liquid inlet and outlet valves 35, 36 (if these are not one-way valves).

Although not shown in FIG. 2, one or more level detectors may be arranged in or at the pump cavity 30 to either continuously measure the level of liquid in the cavity 30 or indicate one or more reference levels in the cavity 30, such as the upper level L2, the lower level L1 or an intermediate level. The output signal of the level detector may be processed to verify proper operation of the pump P1A, P1B. The output signal may also be used as input for controlling of the opening and closing of the air valves 32 (and possibly the inlet and outlet valves 35, 36). Thereby, the stroke volume of the pump P1A, P1B may be precisely controlled.

Figure 3:
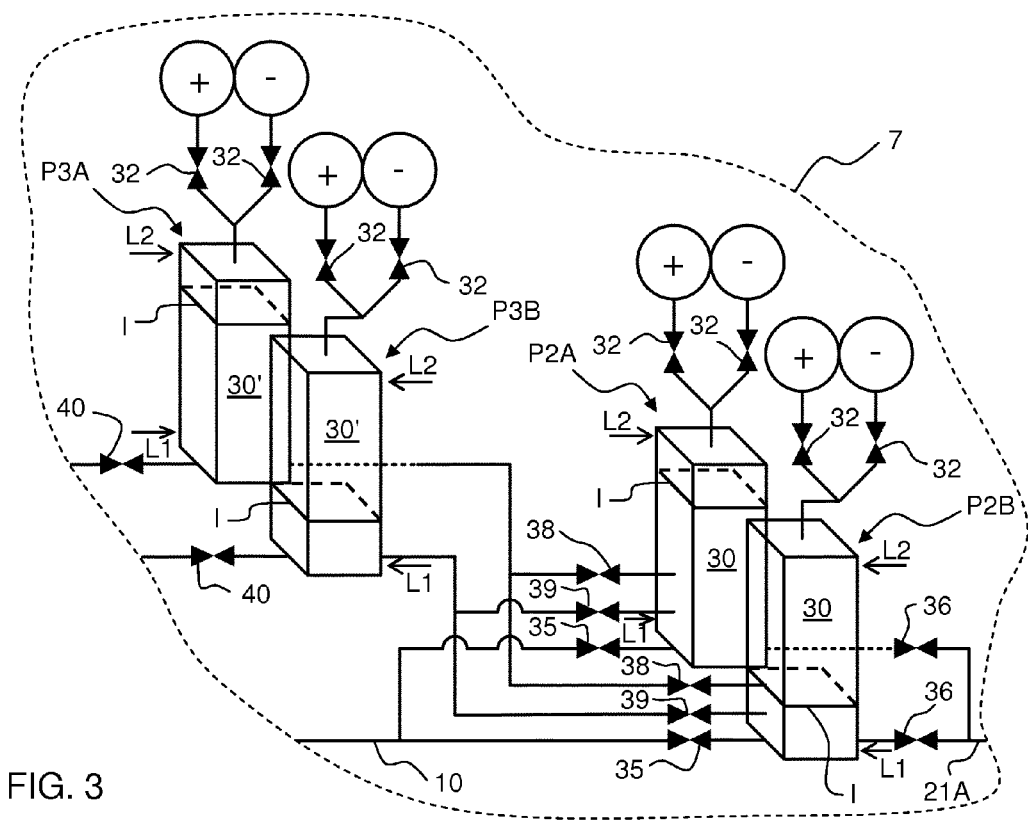
FIG. 3 is a fluid flow-path schematic of an upstream subsystem in the supply arrangement of FIG. 1.

FIG. 3 illustrates an embodiment of the upstream module 7 in FIG. 1. The upstream module 7 comprises a pair of solution pumps P2A, P2B that are connected in parallel and operated in opposite phases to provide a continuous or almost continuous output flow of treatment solution. The solution pumps P2A, P2B are of similar construction as the solution pumps P1A, P1B in the downstream module 6 and utilize a reciprocating gas-liquid interface I driven by an alternately positive and negative gas pressure. Each solution pump P2A, P2B in the upstream module 7 has three liquid inlets and associated inlet valves 35, 38, 39: one inlet for water from the water supply line, and two inlets for two different types of concentrates (acid concentrate and base concentrate). The treatment solution is obtained by mixing the concentrates and water in given proportions. Typically, the concentrates are mixed in small proportions in water, e.g. in the range of 1:30 to 1:50 by volume. In the illustrated embodiment, the mixing takes place in the pump cavity 30. To improve the mixing, it may be advantageous to operate the solution pumps P2A, P2B with a rapid filling phase, so as to induce turbulence in the liquid within the pump cavity 30. The filling phase may therefore be significantly shorter than the emptying phase. Beneficial turbulence may also be promoted by arranging the inlets, and in particular the inlets for the concentrates, above and with a spacing to the lower level L1 in the pump cavity 30.

The upstream module 7 also includes concentrate pumps P3A, P3B that are arranged to meter and pump the respective concentrate to the solution pumps P2A, P2B. The concentrate pumps P3A, P3B are of similar construction as the solution pumps P2A, P2B and utilize a reciprocating gas-liquid interface I (gas-concentrate interface) driven by an alternately positive and negative gas pressure. Each concentrate pump P3A, P3B is formed by a metering cavity 30' with air port and air valves 32. The metering cavity 30' has a concentrate inlet in fluid communication with a concentrate supply (not shown) via a concentrate inlet valve 40, and a concentrate outlet in fluid communication with the pump cavities 30 of the solution pumps P2A, P2B via the inlet valves 38, 39, which thus perform the function of outlet valves for the metering cavities 30'.

The use of concentrate pumps P3A, P3B may serve to improve the accuracy of the proportioned doses of concentrates, and may also serve to reduce the impact of pressure variations in the water inlet line 10 on the proportioned doses. However, in certain implementations, it is conceivable to dispense with one or both concentrate pumps P3A, P3B such that concentrate is drawn directly into the solution pumps P2A, P2B from the concentrate supplies. In another variant, the concentrate pumps P3A, P3B are not integrated in the cassette, but are connected to supply concentrate to the solution pumps P2A, P2B inside the cassette. This allows for the use of advanced concentration pumps. In yet another variant, water and concentrate are at least partially mixed outside the solution pumps P2A, P2B. For example, a dedicated mixing cavity (not shown) may be arranged intermediate the concentrate pumps P3A, P3B and the solution pumps P2A, P2B, whereby the concentrate and water enter and mix in the mixing cavity to form the treatment solution which is then drawn into the solution pumps P2A, P2B. In another example, the concentrate pumps P3A, P3B are connected to pump the concentrates into the water supply line 10, i.e. upstream of the solution pumps P2A, P2B, whereby water and concentrates partially mix in the water supply line 10 before entering the solution pumps P2A, P2B where the water and concentrate are mixed further to form the treatment solution.

It should be noted that care may need to be taken when mixing water and concentrates to avoid mixing the acid and base concentrates before adding water, since this is known to cause precipitation of calcium carbonate. Precipitation may be avoided by spatially separating the concentrates (e.g. different inlets to the pump cavity 30) and/or by temporally separating the delivery of the concentrates to the mixing site (e.g. the pump cavity 30).

Care may also need to be taken to dose the concentrates with sufficient accuracy. As mentioned above, the dose of concentrate is significantly smaller than the dose of water. Accuracy may be improved by configuring the metering cavities 30' to be correspondingly smaller than the pump cavities 30, e.g. by designing the metering cavity 30' with a significantly smaller diameter. For example, the concentrate pump P3A, P3B may be configured to deliver one dose of concentrate by a single or a plurality of full strokes of the gas-concentrate interface I. The use of a plurality of full strokes per dose may improve accuracy further and allow the dose of concentrate to be adjusted with high accuracy by changing the number of full strokes. Alternatively, the dose of concentrate may be adjusted by adjusting the stroke length of the one or more full strokes in the metering cavity 30'.

Air is likely to be present in the incoming water to the solution pumps P2A, P2B. Air and other gaseous substances, such as carbon dioxide, may also be released during the mixing process due the reaction between different substances. It should be noted that these gases are at least partly sucked out of the pumping cavity 30 during the filling phase, since the pump cavity 30 is then in fluid communication with the negative pressure source. This "gas removal process" is an inherent feature of the solution pumps P1A, P1B, P2A, P2B, and also the concentrate pumps P3A, P3B, which may obviate the need to install a separate air removal device upstream of the pumps to ensure accuracy of the pumps. It is conceivable to intermittently perform an enhanced gas removal process in the solution pumps P1A, P1B, P2A, P2B by closing the inlet and outlet valves while opening one of the air valves 32 to communicated the pump cavity 30 with the negative pressure source. This enhanced gas removal process may be performed as a separate step during operation of the pump or be part of the filling phase. It is conceivable that the enhanced gas removal process is followed by a supplementary filling phase, to increase the liquid level in the pump cavity 30 to the upper level L2.

The valves connected to the pump cavity 30 may also be checked for leakage by closing the inlet and outlet valves, and selectively opening one of the air valves 32 to establish a positive or negative pressure in the pump cavity 30. Leakage may be detected by identifying a change in the liquid level in the pump cavity 30, based on the output signal of the level detector(s). A corresponding leakage test may be made for the concentrate pumps P3A, P3B.

It should also be noted that the use of pumps driven by a gas-liquid interface I offers the general advantage of limiting the pressure that may occur in the supply arrangement to the pressures generated by the positive and negative pressure sources. In conventional supply arrangements, the pressure that is generated by the pumps is not inherently limited, leading to a risk for ruptured tubing and connector leakage.

Figure 4:
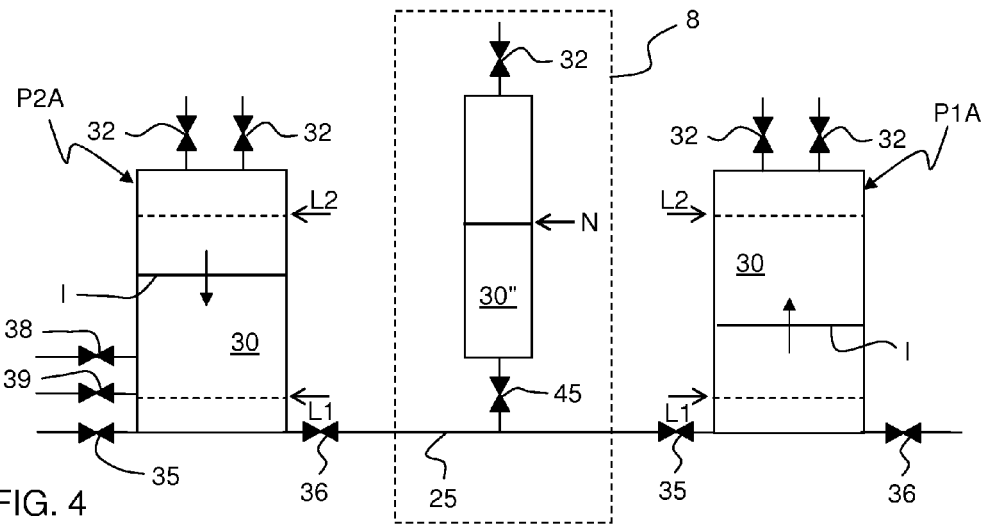
FIG. 4 is a fluid flow-path schematic of calibration subsystem in the supply arrangement of FIG. 1.

FIG. 4 illustrates the taration module 8 as connected for calibration of one solution pump P2A in the upstream module 7 and one solution pump P1A in the downstream module 6. The conductivity cell 20, bypass valve 23 and pressure sensors 22, 27 in FIG. 1 have been omitted for clarity of presentation. The taration module 8 may be operated at start-up of the supply arrangement, and also intermittently during operation of the supply arrangement, to obtain a calibration value between each upstream solution pump P2A, P2B and each downstream solution pump P1A, P1B. It is assumed herein that all of these pumps have similar or identical nominal stroke volume. The taration module 8 is operable to identify any unintended difference in stroke volume between the pumps that e.g. result from manufacturing tolerances or accumulation of deposits in the pump cavities 30.

Even small differences between the actual and nominal stroke volumes of the downstream and upstream solution pumps may lead to a large deviation between the desired UF rate and the actual UF rate that is generated by the supply arrangement. Assume that all pumps have a nominal stroke volume of 100 ml, but that the actual stroke volume deviates from nominal stroke volume by +1% for the downstream pumps P1A, P1B and by −1% for the upstream pumps P2A, P2B. Also assume that the set value for the inlet flow of dialysis fluid to the dialyzer is 500 ml/min, and that the desired UF rate is 500 ml/h and is generated as a flow rate difference between two alternating pairs of upstream and downstream pumps. To achieve the inlet flow, the pumps P1A, P1B, P2A, P2B are set to operate at 2.5 pumping cycles per minute. At this operating frequency, the desired UF rate corresponds to 500/60/2.5=3.33 ml per pumping cycle. However, the actual stroke volumes of the upstream and downstream pumps differ by 2.0 ml (100*1.01-100*0.99). Given that the unintended and desired flow rate differences are of the same magnitude, the supply arrangement may be unable to produce a correct UF rate. The taration module 8 enables the pumps P1A, P1B, P2A, P2B to be relatively calibrated so as to reduce or minimize the unintended flow rate difference.

In FIG. 4, the taration module 8 includes a calibration cavity 30", which has a liquid port connected to the bypass line 25 via a valve 45. The calibration cavity 30" also has an air port, which is connected to ambient via an air valve 32. The calibration cavity 30" is associated with a level detector (not shown) capable of multi-point or continuous detection around a nominal level N in the calibration cavity 30". The nominal level N may be located, as shown, at mid-level in the calibration cavity 30". In a calibration phase, the upstream pump P2A is filled to the upper level L2 and the downstream pump P1A is emptied to the lower level L1, and the calibration cavity 30" is filled to the nominal level N. Then, while the valve 45 and the air valve 32 is open, the upstream pump P2A is activated to perform an emptying stroke and the downstream pump P1A is activated to perform a filling stroke. The emptying stroke ends when the treatment solution reaches the lower level L1, and the filling stroke ends when the treatment solution reaches the upper level L2. Any volumetric difference between the emptying and filling stroke results in a change of the liquid level in the calibration cavity 30". Thus, by detecting any change by the level detector, a calibration value is obtained indicating the current volumetric difference between the pumps P1A, P2A. The skilled person realizes that the calibration values may be applied in many different ways to control the pumps P1A, P1B, P2A, P2B to achieve a correct UF rate in the dialyzer.

An embodiment of the calibration phase is further illustrated in FIGS. 11A-11E during relative calibration of one upstream pump P2A and one downstream pump P1A. Components intermediate the calibration chamber 30" and the pumps P1A, P2A have been omitted for clarity of presentation. For example, the calibration chamber 30" is connected to the pumps P1A, P2A by a bypass line (cf. 25 in FIG. 1). In FIG. 11, white and black fill colours are used to differentiate between closed and open valves, respectively. It is understood that further valves may be installed to control the fluid flow to and from the calibration chamber 30", e.g. corresponding to valves 23, 45 in FIG. 1.

Figure 11A:
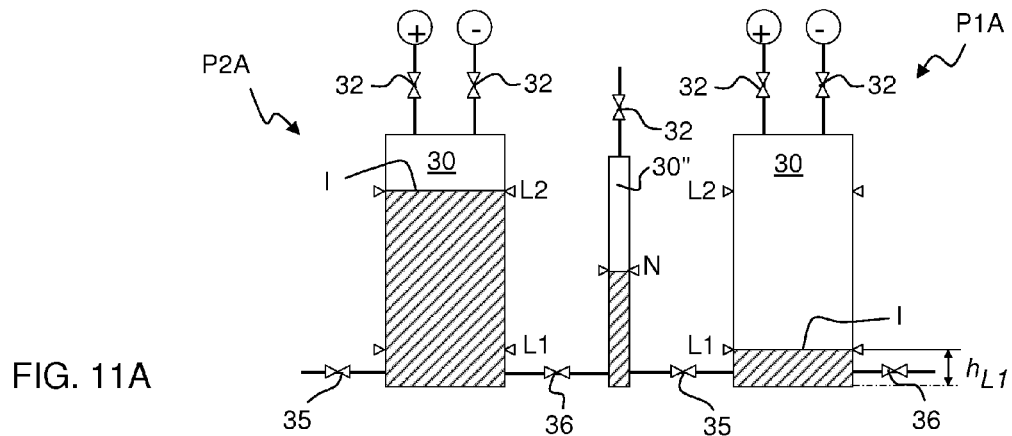
FIGS. 11A-11E illustrate a sequence of fluid states during a calibration phase according to a first example.
Figure 11B:
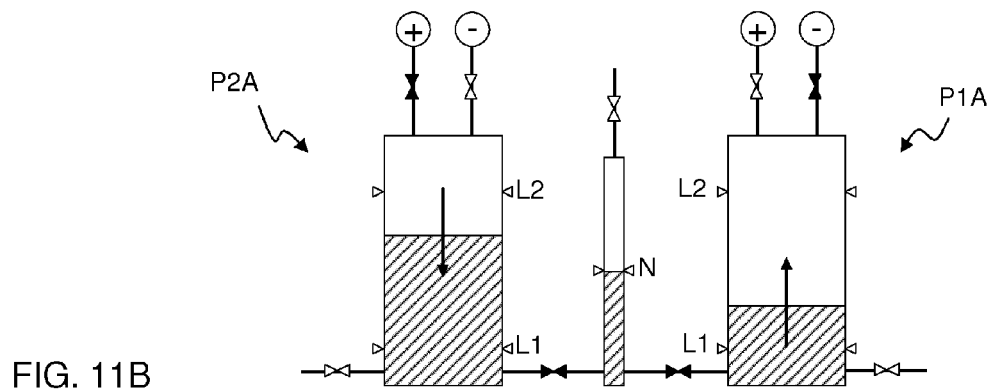
Figure 11C:
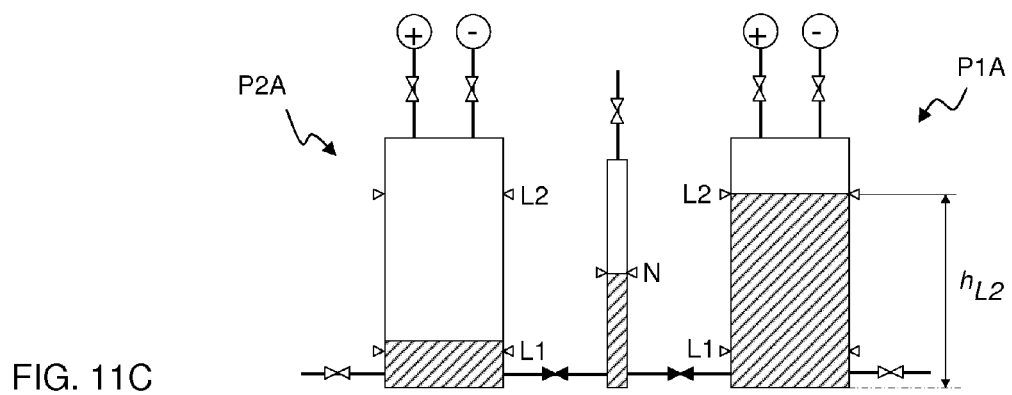
Figure 11D:
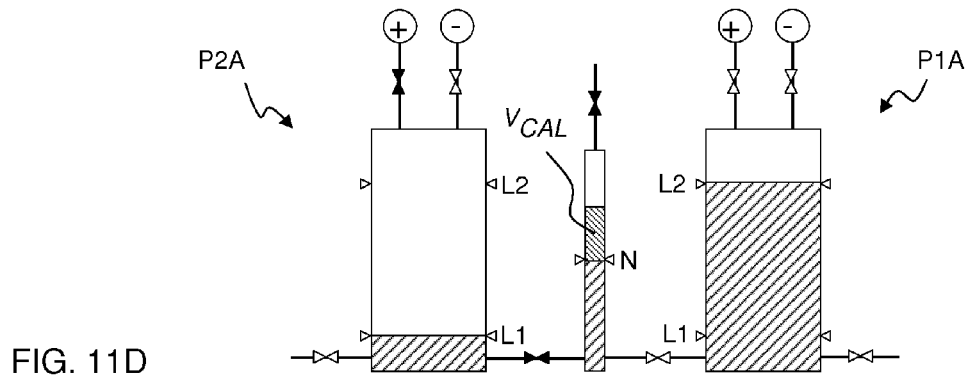
Figure 11E:
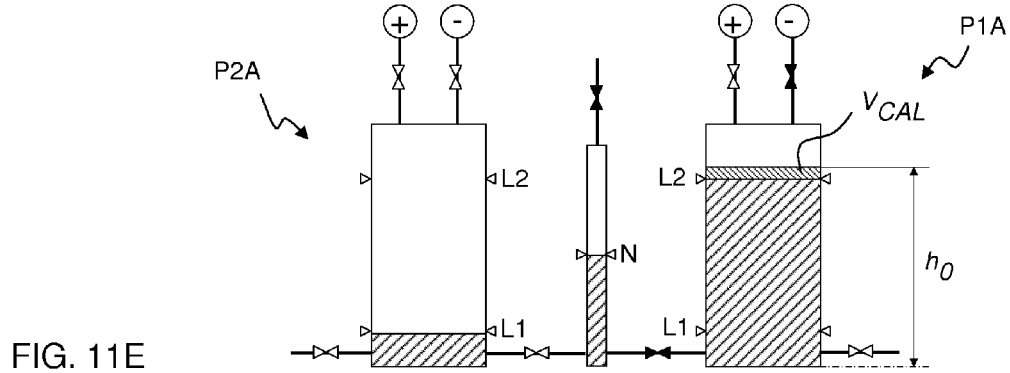

FIG. 11A illustrates the start of the calibration phase. Pump P2A is filled to upper level L2, calibration chamber 30" is filled to level N and pump P1A is filled to lower level L1. The level sensor in pump P1A indicates a height $h_{L1}$ with respect to an origin which may have any location, but coincides with the bottom of pump P1A in the examples given herein. The pumps P1A, P2A are then operated to transfer fluid from pump P2A to pump P1A, without changing the fluid level in the calibration chamber 30" (FIG. 11B), until the fluid level in pump P1A reaches the upper level L2 or the fluid level in pump P2A reaches the lower level L1, whichever occurs first. If the fluid level in pump P1A has reached the upper level L2 (height $h_{L2}$, FIG. 11C), valves are switched such that the fluid flow from pump P2A is instead collected in the calibration chamber 30" until the fluid reaches the lower level L1 in pump P2A (FIG. 11D). If, on the other hand, the fluid level in pump P2A has reached the lower level L1, valves are switched such that the fluid is drawn from the calibration chamber 30" into pump P1A until the fluid reaches the upper level L2 in pump P1A (height $h_{L2}$). Thus, any difference in nominal stroke volume between the pumps P1A, P2A results in a level change in the calibration chamber 30". Then, valves are switched (if necessary) such that pump P1A is operated to restore the fluid level at level N in the calibration chamber 30", resulting in height $h_0$, in pump P1A (FIG. 11E). The height $h_0$, represents the fluid level in pump P1A that balances the actual stroke volumes of the pumps P1A, P2A and may be denoted a "balancing level" or "balancing height".

Figure 11F:
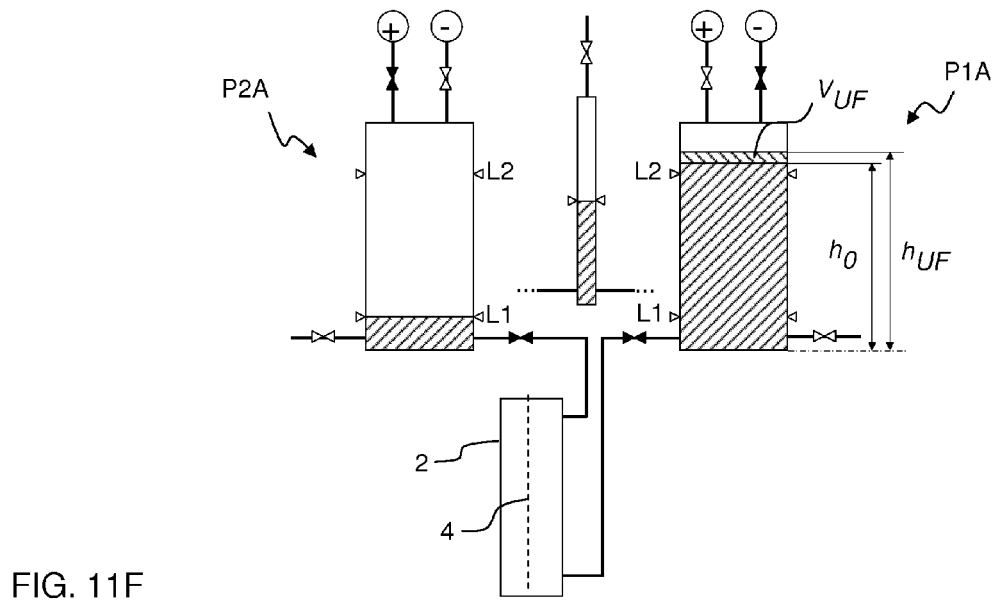
FIG. 11F illustrates a fluid state when the supply arrangement is operatively connected to a dialyzer.

During the calibration phase, at least heights $h_0$, and $h_{L2}$ are measured in pump P1A, and the level change from level N in the calibration chamber 30" is measured by any suitable technique. The volumetric difference between the pumps P1A, P2A forms a "calibration volume", denoted $V_{CAL}$, which is computed based on the level change in the calibration chamber 30". The calibration volume $V_{CAL}$ is positive for an increased level in the chamber 30" and negative for a decreased level in the chamber 30". As shown in FIG. 11F, the pumps P1A, P2A are controlled to yield a desired UF rate when connected to the dialyzer 2, by adjusting the final upper fluid level in pump P1A to a height value $h_{UF}$ which is computed as a function of the calibration data ($h_0$, $h_{L2}$, $V_{CAL}$). The calibration data is related according to:

$$V_{CAL}=(h_0-h_{L2})\cdot A \quad (1)$$

where A is the cross-sectional area of pump P1A. The desired difference volume $V_{UF}$ between the pumps P2A and P1A is given by:

$$V_{UF}=(h_{UF}-h_0)\cdot A \quad (2)$$

This yields a functional relation between the height value $h_{UF}$ and the desired difference volume $V_{UF}$:

$$h_{UF} = \frac{V_{UF}}{A} + h_0 = \frac{V_{UF}}{V_{CAL}} \cdot (h_0 - h_{L2}) + h_0 = \frac{V_{UF}}{V_{CAL}} \cdot \Delta h + h_0 \quad (3)$$

where $\Delta h$ is the level change in pump P1A corresponding to the calibration volume $V_{CAL}$. In other words, the stroke length of pump P1A is adjusted by shifting the final upper level from the balancing height $h_0$, by a distance $\Delta h_{UF}=h_{UF}-h_0=V_{UF}/V_{CAL}\cdot\Delta h$.

Although not shown in FIG. 11, it is conceivable that one or more dedicated valves may be arranged in the bypass line to control of the flow of treatment solution into and out of the calibration cavity 30" during the calibration phase, similar to valve 45 in FIG. 4. This valve may be closed at the start of the calibration phase and is only opened (together with air valve 32, if not already open) when the treatment solution reaches the lower level L1 in pump P2A and when the treatment solution reaches the upper level L2 in pump P1A, whichever occurs first. Thereby, the calibration cavity 30" is selectively opened only to receive/deliver the calibration volume $V_{CAL}$.

In one of many variants, the downstream and upstream pumps P1A, P2A are operated in sequence during the calibration phase. For example, in FIG. 4, the inlet valve 35 of the downstream pump P1A may be closed during the emptying phase of the upstream pump P2A, while the valve 45 and the air valve 32 of the calibration cavity 30" are open, such that the treatment solution is pumped into the calibration cavity 30". Similarly, the outlet valve 36 of the upstream pump P2A may be closed during the filling phase of the downstream pump P1A, while the valve 45 and the air valve 32 of the calibration cavity 30" are open, such that the treatment solution is drawn out of the calibration cavity 30" into the downstream pump P1A. This variant requires the volume of the calibration cavity 30" to be at least equal to the stroke volume of the upstream pump P2A.

One potential limitation of the calibration technique described above with reference to FIGS. 4 and 11 is that it requires reliable detection of a relatively small level change in the downstream pump P1A, specifically the difference between the upper height $h_{L2}$ (FIG. 11C) and the balancing height $h_0$, (FIG. 11E).

To improve the accuracy, the calibration data may be obtained as an average over a number of calibration phases. It is also conceivable that the calibration phase includes a plurality of transfers of treatment solution from pump P2A to pump P1A, such that the volumetric difference for a plurality of transfers is accumulated in the calibration cavity 30", and that this accumulated volume is then finally transferred to pump P1A to yield an upper level therein. This variant may require the calibration cavity 30" to be larger, so as to accommodate the accumulated volumetric difference.

It is also possible to increase the accuracy by redesigning the calibration phase so as to increase the calibration volume $V_{CAL}$ transferred from the calibration chamber 30" to the downstream pump P1A during the calibration phase. Such an embodiment is further illustrated in FIGS. 12A-12G. Structurally, the system in FIG. 12 only differs from the system in FIG. 11 in that the calibration chamber 30" is designed to contain a large and well-defined volume of fluid between an upper reference level L2" and a lower reference level L1". In the illustrated example, the calibration chamber 30" is designed as a pipette. The majority of the volume contained within the calibration chamber 30" is defined within a central bulb portion, and the lower and upper levels L1", L2" are detected in a respective capillary tube portion 30a, 30b connected to the bulb portion.

Figure 12A:
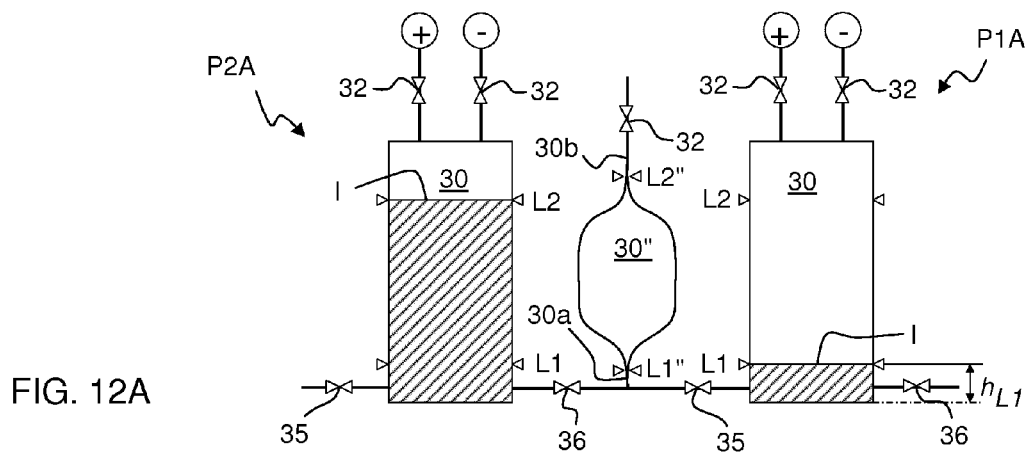
FIGS. 12A-12G illustrate a sequence of fluid states during a calibration phase according to a second example.
Figure 12B:
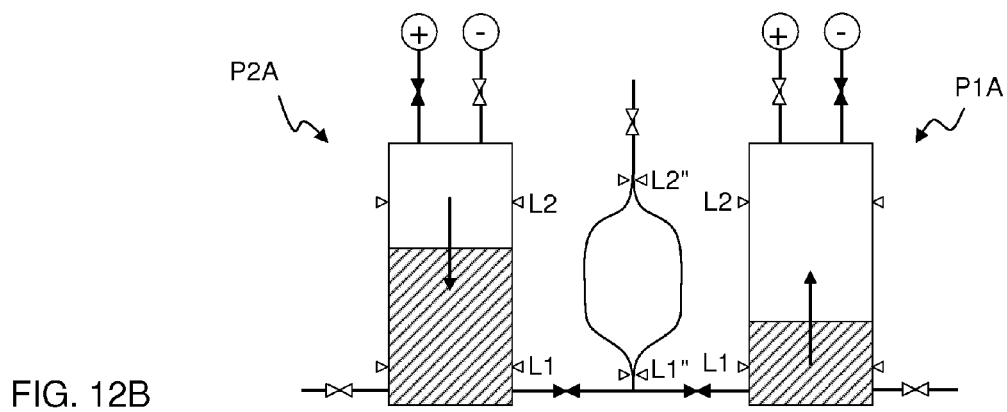
Figure 12C:
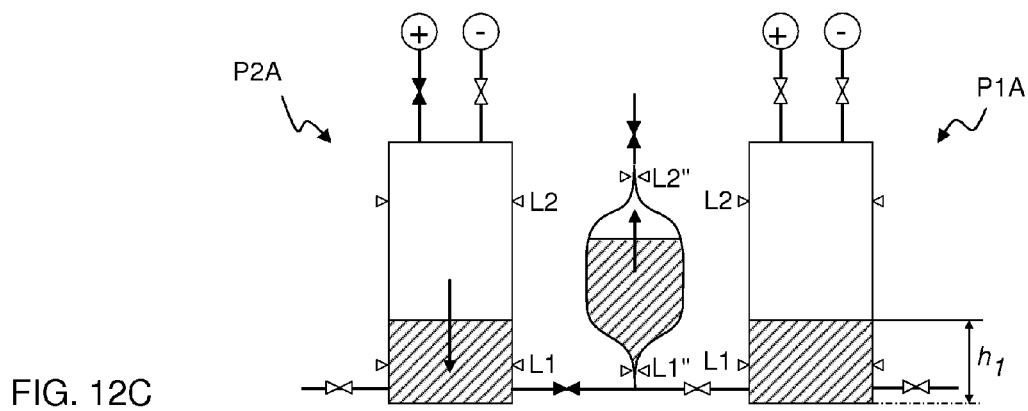
Figure 12D:
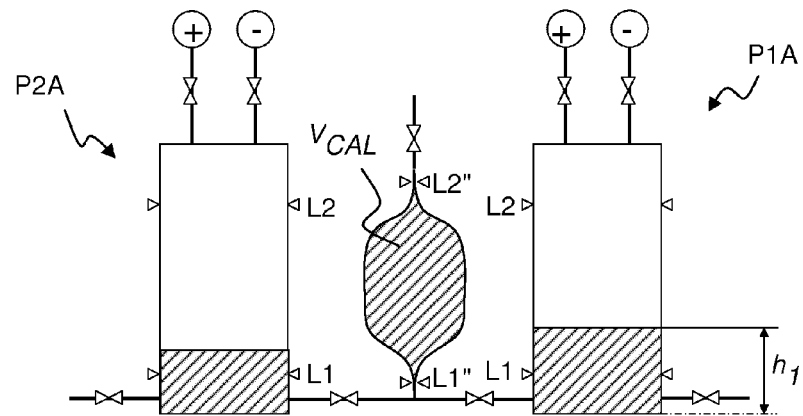
Figure 12E:
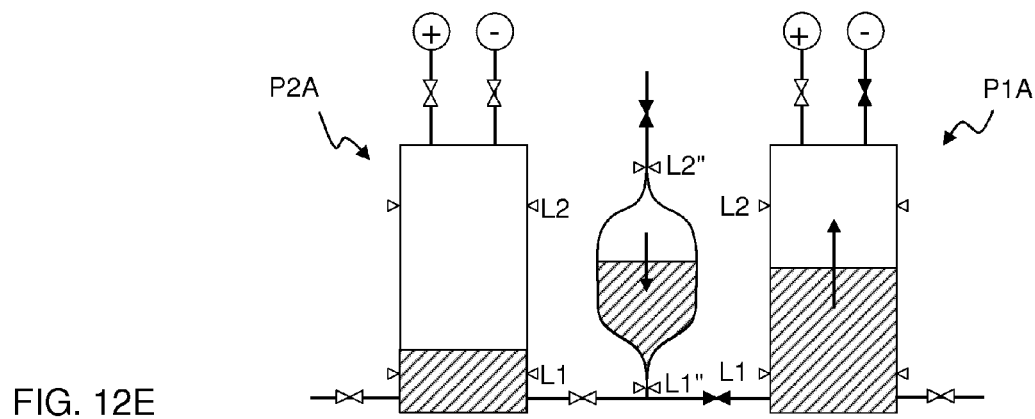
Figure 12F:
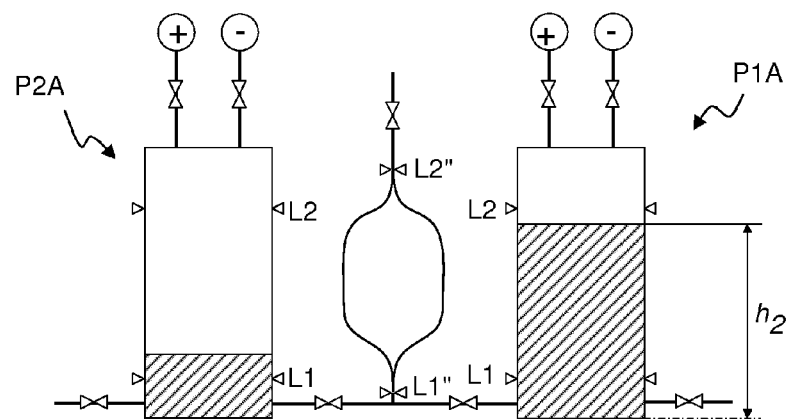
Figure 12G:
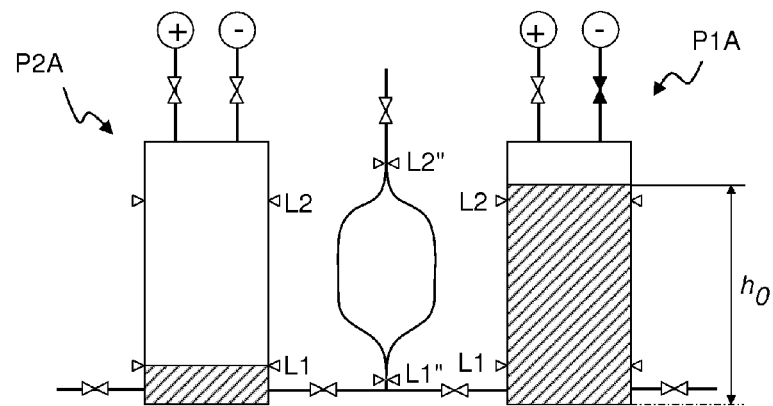

FIG. 12A illustrates the start of the calibration phase. Pump P2A is filled to its upper level L2, calibration chamber 30" is at its lower level L1", and pump P1A is filled to its lower level L1. The level sensor in pump P1A indicates a height $h_{L1}$ with respect to a predefined origin. The pumps P1A, P2A are then operated to pump fluid from pump P2A to pump P1A, without increasing the fluid level in the calibration chamber 30" (FIG. 12B). At a chosen time during the emptying stroke of pump P2A, valves are switched to direct the fluid from pump P2A into the calibration chamber 30" instead of into pump P1A. Thereby, the fluid remains at a first height $h_1$ in pump P1A while the calibration chamber 30" is being filled (FIG. 12C). This height $h_1$ is measured. When the calibration chamber is filled to level L2" (FIG. 12D), valves are switched such that pump P1A draws the fluid from the calibration chamber 30" (FIG. 12E). When the fluid in the calibration chamber 30" reaches level L1", a second height $h_2$ of the fluid level in pump P1A is measured (FIG. 12F) and valves are switched to establish communication between the pumps P1A and P2A, while closing off the calibration chamber 30", and to cause pump P1A to draw fluid from pump P2A until the fluid reaches the lower level in pump P2A. At this time, a balancing height $h_0$, in pump P1A is measured (FIG. 12G), and the calibration phase is completed.

Figure 12H:
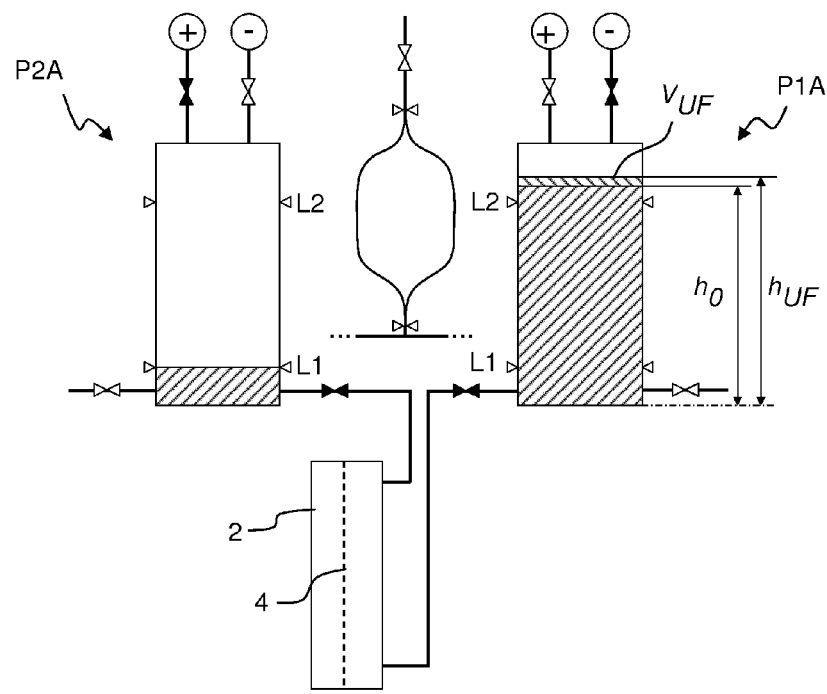
FIG. 12H illustrates a fluid state when the supply arrangement is operatively connected to a dialyzer.

During the calibration phase, heights $h_0$, $h_1$ and $h_2$ are measured in pump P1A. The calibration volume $V_{CAL}$ is known and predefined. As shown in FIG. 12H, the pumps P1A, P2A are controlled to yield a desired UF rate when connected to the dialyzer 2, by adjusting the final upper level in pump P1A to a height value $h_{UF}$ which is computed as a function of the calibration data ($h_0$, $h_1$, $h_2$ and $V_{CAL}$). In analogy with Equation (3) above, the control is based on the following functional relation between the desired height value $h_{UF}$ and the desired difference volume $V_{UF}$:

$$h_{UF} = \frac{V_{UF}}{V_{CAL}} \cdot (h_2 - h_1) + h_0 = \frac{V_{UF}}{V_{CAL}} \cdot \Delta h + h_0 \qquad (4)$$

where $\Delta h$ is the level change in pump P1A corresponding to the calibration volume $V_{CAL}$. Like in the embodiment in FIG. 11, the stroke length of pump P1A is adjusted by shifting the final upper level from the balancing height $h_0$, by a distance $\Delta h_{UF} = h_{UF} - h_0 = V_{UF}/V_{CAL} \cdot \Delta h$.

The level measurements in pump P1A during the calibration phase also makes it possible to determine the actual inlet flow of treatment solution to the dialyzer 2 with high accuracy. This inlet flow is given by the actual stroke volume of pump P2A, which is equal to the stroke volume $V_0$ of pump P1A when operated to reciprocate the interface I between heights $h_0$, and $h_{L1}$:

$$V_0 = V_{CAL} \cdot (h_0 - h_{L1})/(h_2 - h_1) \qquad (5)$$

In the foregoing examples, the desired UF rate is set by adjusting the stroke length of the downstream pump P1A, based on calibration data, while the upstream pump P2A is operated between its reference levels L1, L2. In an alternative, the desired UF rate is set by adjusting the stroke length of the upstream pump P2A while the downstream pump P1A is operated between its reference levels L1, L2. Such adjustment requires that the height values in the calibration data are measured in the upstream pump P2A during the calibration phase. This may be achieved by implementing a "reversed" calibration phase, which involves transferring fluid from the downstream pump P1A to the upstream pump P2A. The foregoing description is equally applicable, with the difference that the heights are determined in the upstream pump P2A and used for computing the final upper height $h_{UF}$ that yields the desired UF rate. Alternatively, the heights may be measured in the upstream pump P2A during the (non-reversed) calibration phase as shown in FIGS. 11-12 and used for calculating a height $h_{UF}$ of the final lower fluid level in pump P2A to yield the desired difference volume $V_{UF}$. Equations (3) and (4) are applicable for computing $h_{UF}$ in such an embodiment if the balancing height $h_0$, and the level change $\Delta h$ are measured in pump P2A.

However, it should be noted that it may be desirable to design the upstream module 7 (FIGS. 1 and 3), and thus the upstream pumps P2A, P2B, to supply a constant flow of treatment solution to the dialyzer 2. The complexity of the upstream module 7 may increase if it needs to deliver momentarily changing flow rates of treatment solution, especially if the upstream module 7 is configured to prepare the treatment solution by mixing liquid concentrates with water. It may therefore be preferable to control the UF rate by adjusting the stroke length of the downstream pumps P1A, P1B.

In all examples above, the desired UF rate is set by adjusting the final upper level in the downstream pumps P1A, P1B. It is realized that the desired UF rate may alternatively be set by adjusting the final lower level in the downstream pumps P1A, P1B, based on the calibration data.

Figure 5A:
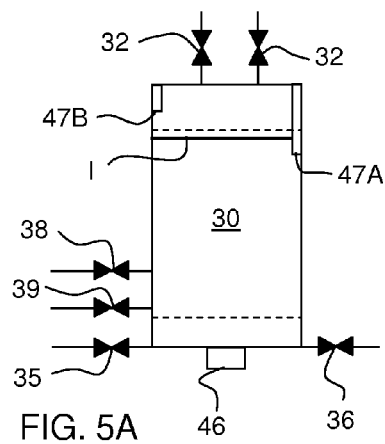
FIG. 5A is a section view of a pump in the supply arrangement of FIG. 1.
Figure 5B:
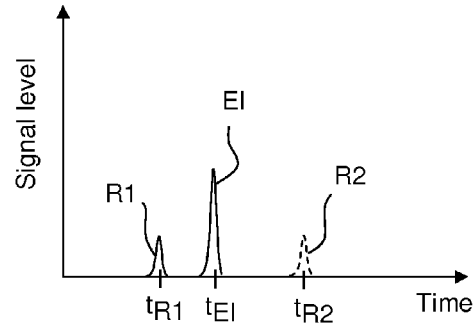
FIG. 5B is a plot of an output signal of an ultrasound transceiver in the pump of FIG. 5A.

FIG. 5A illustrates an embodiment of an ultrasonic level detector 46 capable of continuous level detection. In the illustrated example, the level detector 46 is installed in a solution pump, but it may be equally applicable in the calibration cavity 30" and/or the concentration pumps. The level detector 46 is formed by an ultrasound transceiver which is arranged at the bottom of the cavity 30 to generate and detect ultrasonic waves in the cavity 30. The liquid level is determined, e.g. by the controller that operates the supply arrangement, based on the time difference (travelling time) between ultrasonic emission and receipt of an ultrasonic wave (echo) generated by reflection at the gas-liquid interface I. In the example of FIG. 5A, lugs 47A, 47B are formed in the wall of the cavity 30 to define reflection surfaces to the ultrasonic waves around a nominal top level (dashed line). As shown in FIG. 5B, the lugs 47A, 47B produce reference echoes R1, R2 in the output signal of the transceiver 46. Since the reference echoes R1, R2 correspond to fixed locations in the cavity 30, the location of the gas-liquid interface I may be precisely determined by relating the echo EI from the interface I to the reference echoes R1, R2. Assuming that the speed of sound is the same in the treatment solution between lugs 47A, 47B, the location of the interface I may be determined by interpolation, e.g. linear interpolation, between the fixed locations of the lugs 47A, 47B. Since the speed of sound may vary in the treatment solution between the fixed locations, an average speed of sound may be first calculated according to: $C_{av}=L_{R1}/t_{R1}+L_{R2}/t_{R2}$, where $L_{R1}$, $L_{R2}$ are the distances from the transceiver 46 to the lugs 47A and 47B, and $t_{R1}$, $t_{R2}$ are the time differences for the reference echoes R1, R2. The location of the interface I may then be obtained as: $L_{EI}=C_{av}\cdot t_{EI}/2$, where $t_{EI}$ is the time difference for the echo EI.

It is understood that the controller may perform the determination of the reference echoes R1, R2 only intermittently during operation the supply arrangement, e.g. at startup or at regular intervals, and then determine the liquid level using the recorded time differences $t_{R1}$, $t_{R2}$, until the next determination of the reference echoes R1, R2. To record the reference echo R2, the liquid level needs to be raised above the upper lug 47B.

The lugs 47A, 47B may have other placements in the cavity 30. For example, the upper lug 47B may be located near, e.g. below, the upper level, L2, and the lower lug 47A lug may be located near, e.g. above, the lower level L1. More than two lugs may be provided in the cavity 30, and the above computations are readily extended to such an implementation.

In a further variant, only one lug is formed on the wall of the cavity 30, preferably between the lower and upper levels L1, L2. The controller may determine the liquid level by assuming that the speed of sound is the same around the lug, $L_{EI}=t_{EI}\cdot L_R/t_R$, where $L_R$, is the distance from the transceiver 46 to the single lug, and $t_R$ is the time difference for the corresponding reference echo R.

It is also conceivable that the controller implements any combination of the above-described uses of one and two reference echoes.

Figure 6A:
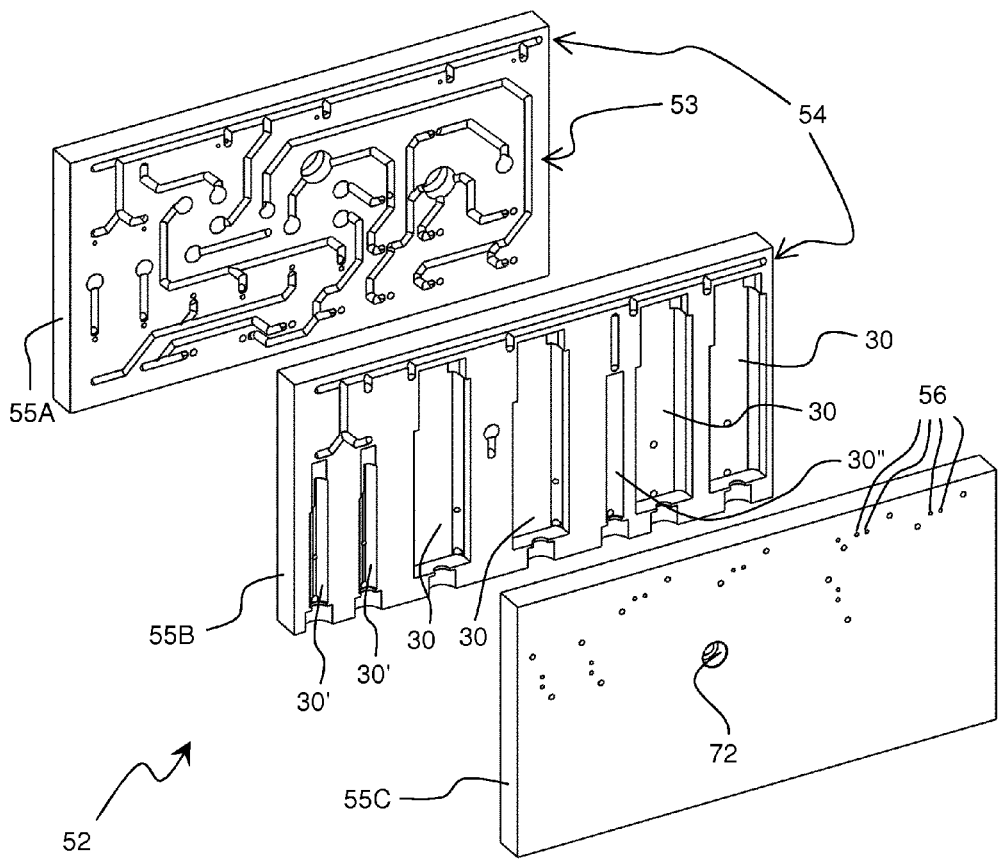
FIG. 6A is an exploded perspective view of a cassette that implements part of the supply arrangement in FIG. 1.
Figure 6B:
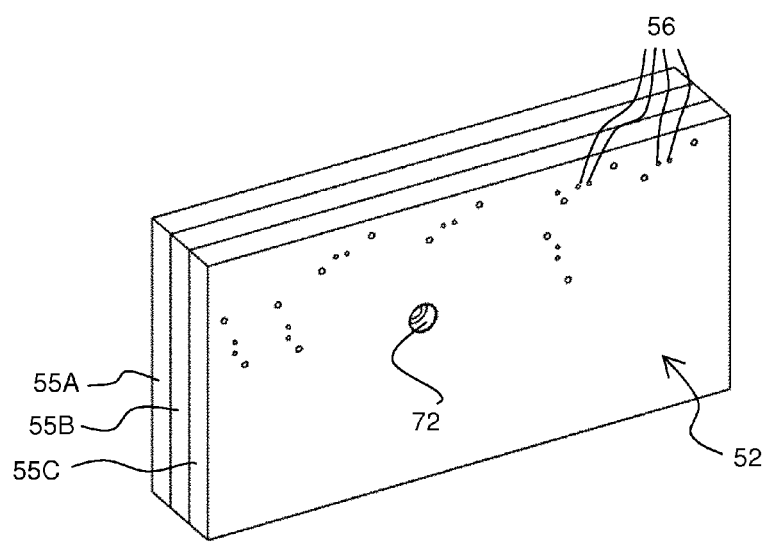
FIG. 6B is an assembled perspective view of the cassette in FIG. 6A.
Figure 7A:
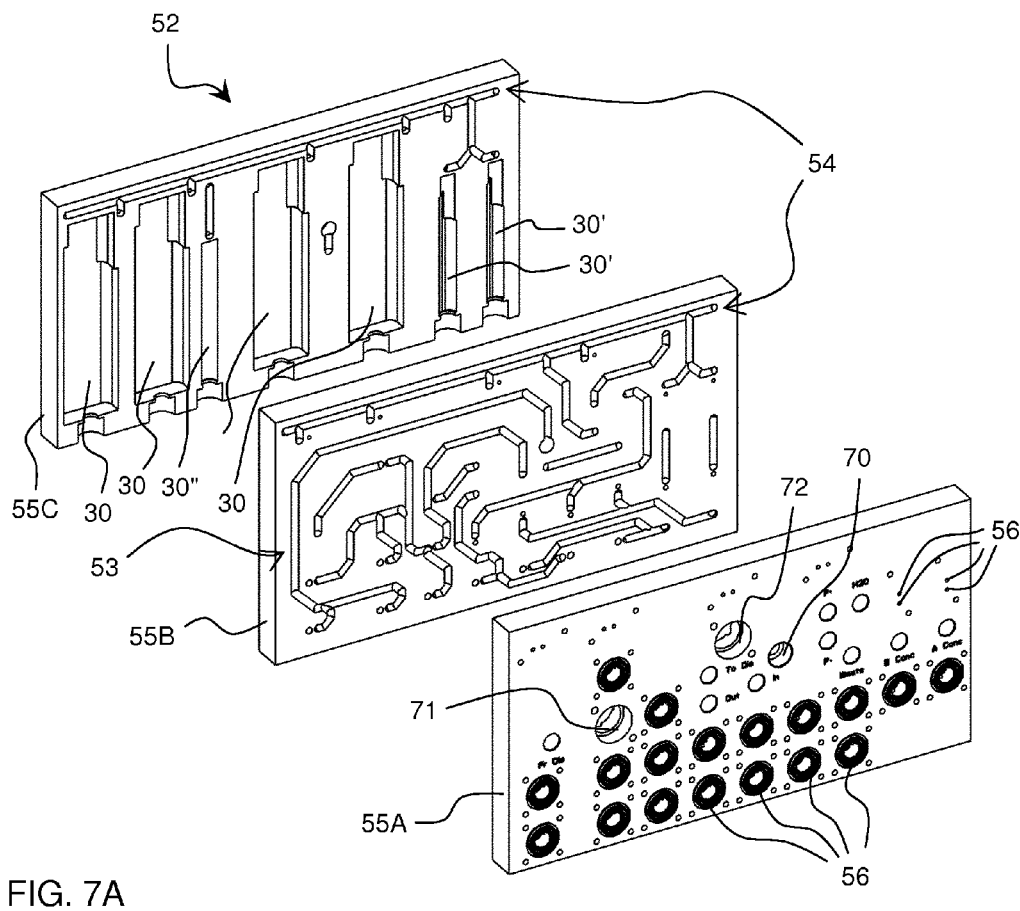
FIG. 7A is an exploded perspective view of the cassette in FIG. 6A, taken from an opposite direction.
Figure 7B:
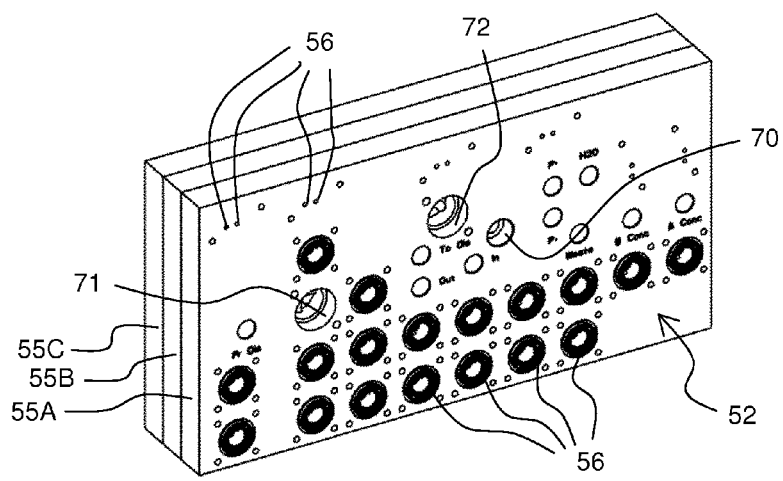
FIG. 7B is an assembled perspective view of the cassette in FIG. 7A.

FIGS. 6-8 illustrate the structure of a cassette 50 that integrates the downstream module 6, the upstream module 7 and the taration module 8 of FIG. 1, as well as certain of the sensors/detectors. FIGS. 6B and 7B are perspective views taken from opposite directions of a body 52 of plastic material that defines a plurality of internal channels and cavities, and FIGS. 6A and 7A are corresponding exploded perspective views illustrating the body 52 before assembly. The body 52 defines a hydraulic manifold 53 in the form of internal liquid channels that distribute liquid (water, concentrates and treatment solution) to and between the cavities 30, 30', 30" of the modules 6-8 in FIG. 1. The body 52 also defines a pneumatic manifold 54 in the form of internal pneumatic channels that distribute pneumatic pressure to the pumps P1A, P1B, P2A, P2B, P3A, P3B in the modules 6 and 7 in FIG. 1. The body is formed by three rectangular plates 55A, 55B, 55C of solid plastic material which are sealingly assembled, e.g. by diffusion bonding, into a compact block in the shape of a cuboid, in this example a rectangular cuboid. As seen in FIGS. 6A and 7A, the channels and cavities are formed by cooperating recesses in the faces of the plates 55A-55C, such that the partition planes between the plates 55A-55C intersects the respective channels and cavities. One pair of plates (55A and 55B) defines the hydraulic manifold 53 and part of the pneumatic manifold 54 (channels for positive pressure), and the other pair of plates (55B and 55C) defines the cavities 30, 30', 30" of the modules 6-8 and part of the pneumatic manifold 54 (channels for negative pressure). By arranging all cavities 30, 30', 30" around one partition plane it is possible to manufacture certain faces of the plates 55A-55C with higher tolerances, e.g. the faces that define the cavities 30, 30', 30". The separation of the hydraulic manifold 53 from the cavities 30, 30', 30" may facilitate design and manufacture. It may also facilitate optimization of the extent (length) of the hydraulic manifold 53 and the pressure drop in the hydraulic manifold 53.

Figure 8A:
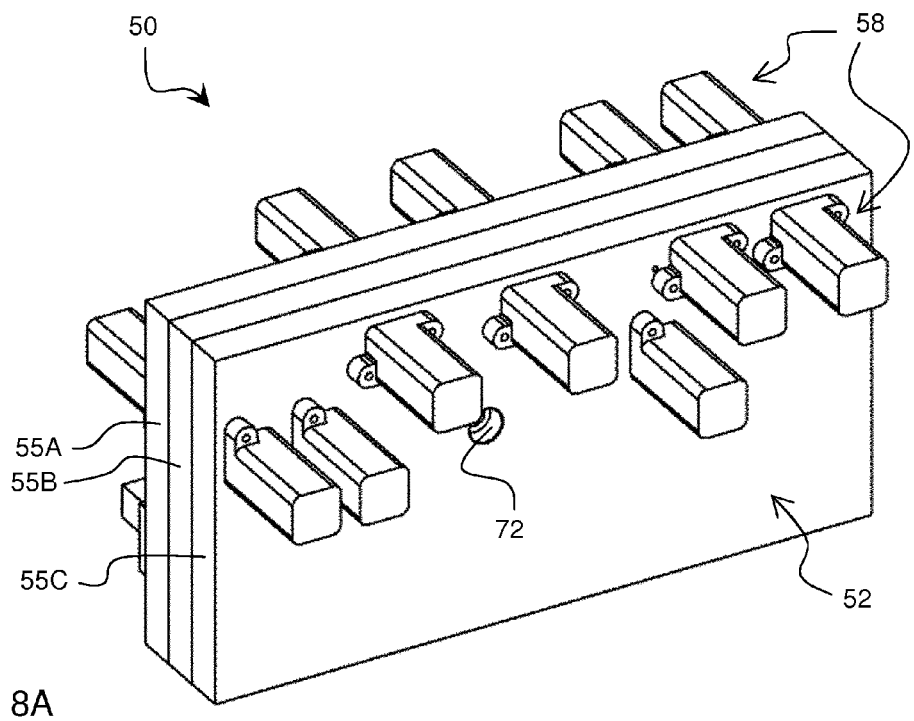
FIGS. 8A-8B are perspective views of the cassette in FIG. 6B and FIG. 7B, respectively, with valves attached.
Figure 8B:
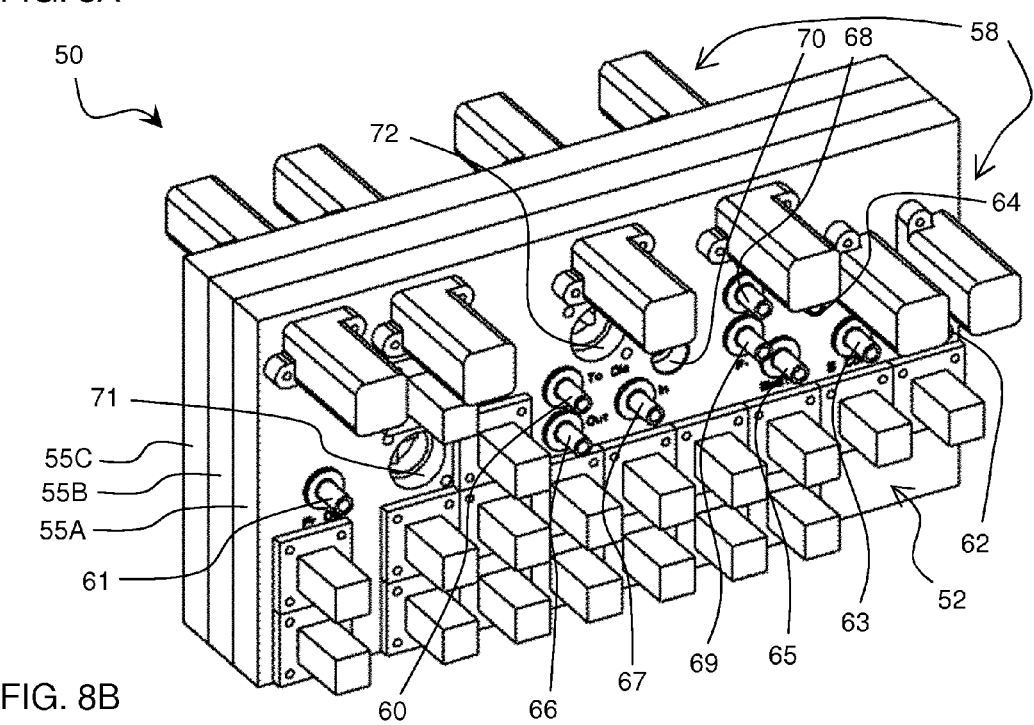

The external faces of the body 52 defines valve ports 56 for mounting of the air valves 32, inlet and outlet valves 35, 36, 38, 39, bypass valve 23, intermediate system valves 24A, 24B and valve 45 (collectively designed as a valve arrangement by reference number 58 in FIGS. 8A-8B). In the illustrated embodiment, all valves are 2-way solenoid valves that are normally closed. The choice of normally closed valves ensures that the valves are closed in the event of a power failure. The valves may be of any conceivable type, such as a top mounted valve with integrated valve seat which is mounted onto the valve port 56, a sub-top mounted valve that is mounted on top of a valve seat integrated in the valve port 56, or a cartridge valve which is inserted in one piece into the valve port 56. As seen in FIG. 8B, the body also includes a number of connectors providing fluid communication to the hydraulic manifold 53, including dialyzer connectors 60, 61 for connection to the dialyzer inlet and outlet, concentrate connectors 62, 63 for connection to the supplies for acid and base concentrates, a water connector 64 for connection to the water supply line 10, a waste connector 65 for connection to the third solution line 21C, and cell connectors 66, 67 for connection to the inlet and outlet of the conductivity cell 29. The body 52 also has pneumatic connectors 68, 69 in communication with pneumatic manifold 54 for connection to the positive and negative pressure sources. The body 52 in FIGS. 6-8 is also provided with holes 70, 71, 72 for mounting the pressure sensors 22, 28 and the blood leak detector 29 in contact with the hydraulic manifold 53.

Figure 9A:
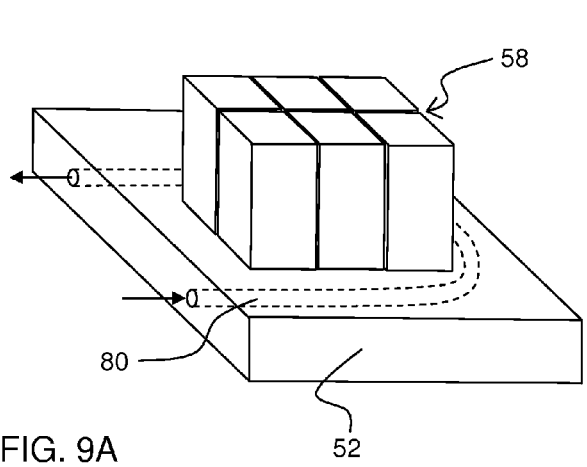
FIGS. 9A-9B are perspective and plan views of embodiments for cooling of valves.
Figure 9B:
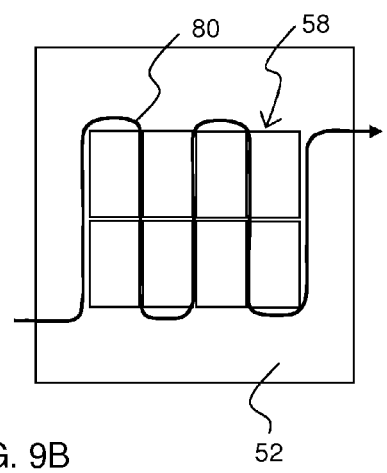

FIGS. 9A-9B illustrate two embodiments of a cassette 50 with a hydraulic manifold that includes a dedicated cooling or heat dissipation channel 80 for diverting heat from the valves 58 and the body portion where the valves 58 are mounted. The cooling channel 80 may be connected in the water supply line 10, such that the heat from the valves 58 is used for pre-heating the incoming water. In the perspective view of FIG. 9A, the cooling channel 80 extends around the valve mounting portion. In the top plan view of FIG. 9B, the cooling channel 80 forms a meandering pattern across the mounting portion.

Figure 10:
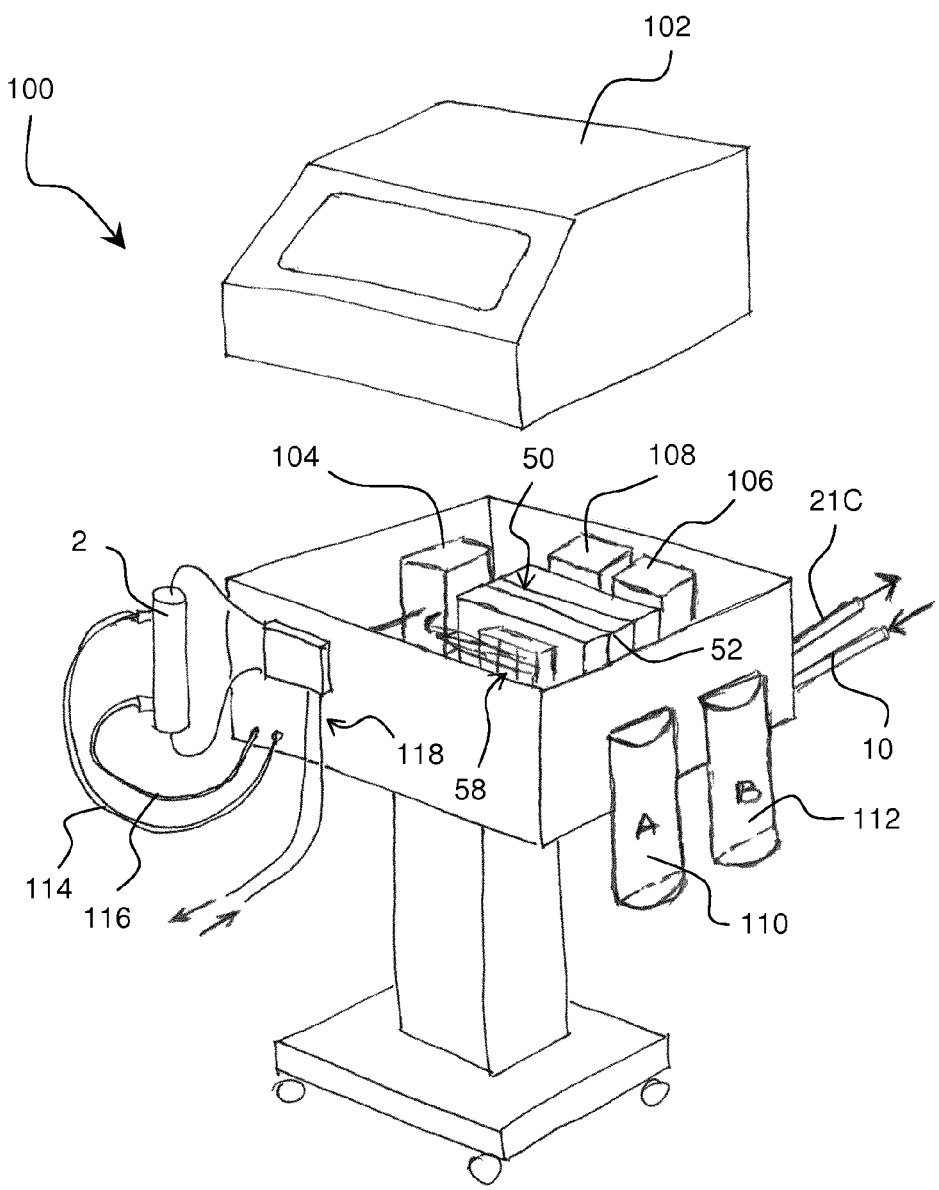
FIG. 10 is a perspective view of a dialysis monitor containing a cassette that implements part of the supply arrangement of FIG. 1.

FIG. 10 shows a schematic example of a dialysis machine or dialysis monitor 100 that includes a cassette 50 as described in the foregoing. A top cover 102 of the machine 100 has been removed to make the machine interior visible. The machine 100 has a controller 104 which is electrically connected to the cassette 50 to control the switching of the valve arrangement 58 and to retrieve data from various sensors/detectors in the machine, including the level detectors associated with the pump chambers and the calibration chamber. The controller 104 also performs the relative calibration of the solution pumps using the taration module 8 and sets the stroke lengths of the solution pumps accordingly to generate a desired UF rate in the dialyzer 2. The controller 104 may perform additional functions, e.g. operating a blood pump, and performing various safety functions, etc. The controller 104 may be implemented as a computer that executes dedicated program instructions. Positive and negative pressure sources 106, 108 are pneumatically connected to the cassette 50. Reservoirs 110, 112 for acid and base concentrate, respectively, are mounted on the machine 100 in fluid communication with the cassette 50. Water supply line 10 and waste line 21C are connected in fluid communication with the cassette 50. A dialyzer 2 is connected to dialysis lines 114, 116 that extend to the dialyzer connectors (60, 61 in FIGS. 8A-8B) on the cassette 50. An extracorporeal blood flow circuit 118 is attached to the machine 100, such that a blood pump (not shown) in the machine 100 is operable to circulate blood from a patient, through the dialyzer 2 and back to the patient.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

For example, the cassette may be installed to supply treatment solution in any type of dialysis system, including systems for hemodialysis, hemodiafiltration, hemofiltration, ultrafiltration (fluid removal), etc.

The cassette may be configured to implement any combination of upstream, downstream and taration modules. Further, the solution pumps need not be connected in parallel pairs, but a single solution pump may be used instead. As a further alternative, more than two solution pumps may be connected in parallel in the upstream and/or downstream modules.

The invention claimed is:

1. A cassette for pumping a treatment solution through a dialyzer in a dialysis system, said cassette comprising:
   a body,
   a hydraulic manifold which is defined inside the body and configured for fluid communication with a first hydraulic connector on the body, the first hydraulic connector being arranged for connecting the dialyzer to the cassette,
   a pneumatic manifold which is defined inside the body and configured for fluid communication with a first pneumatic connector on the body, the first pneumatic connector being arranged for connecting the cassette to a pneumatic pressure source,
   a set of solution pumps including an upstream solution pump and a downstream solution pump, each solution pump of the set of solution pumps including a pump cavity which is defined inside the body for fluid communication with the hydraulic and pneumatic manifolds,
   a calibration cavity connected for fluid communication with a bypass line that extends between the upstream and downstream solution pumps, and
   a valve arrangement which is operable to selectively communicate the pump cavity with the hydraulic and pneumatic manifolds so as to, during the operation of the respective solution pump, reciprocate an interface in the pump cavity and thereby displace the treatment solution through the hydraulic manifold,
   wherein each of the pump cavities defines, during operation of the respective solution pump, said interface as a direct gas-to-liquid interface in the pump cavity between a gaseous substance admitted via the pneumatic manifold and the treatment solution admitted via the hydraulic manifold, and
   wherein the cassette is operable in a calibration phase, in which the valve arrangement is operable to cause one of the upstream or downstream solution pumps to perform an emptying stroke that moves the direct gas-to-liquid interface from an upper reference level to a lower reference level so as to push the treatment solution into the bypass line, cause the other of the upstream or downstream solution pumps to perform a filling stroke that moves the direct gas-to-liquid interface from a lower reference level to an upper reference level so as to draw the treatment solution from the bypass line, and selectively establish fluid communication between the bypass line and the calibration cavity during the emptying and filling strokes so as to transfer a known or measurable calibration volume between the calibration cavity and the pump cavity of the upstream solution pump or the downstream solution pump, wherein a level detector is operable to measure a level change corresponding to the calibration volume in said pump cavity of the upstream solution pump or the downstream solution pump.

2. The cassette of claim 1, which includes an upstream subsystem for providing the treatment solution to the dialyzer via the first hydraulic connector, and a downstream subsystem for pumping the treatment solution from the dialyzer via a second hydraulic connector on the body, wherein the upstream subsystem includes the upstream solution pump and the downstream subsystem includes the downstream solution pump.

3. The cassette of claim 1, wherein the cassette further includes a calibration subsystem for relatively calibrating the upstream solution pump and the downstream solution pump, wherein the calibration subsystem includes the calibration cavity which is defined inside the body and connected for fluid communication with the bypass line that extends between the upstream and downstream solution pumps, wherein level detectors are associated with the upstream and downstream solution pumps to indicate levels of the treatment solution in the respective pump cavity, wherein the cassette is operable to reciprocate the direct gas-to-liquid interface between an upper level and a lower level in the respective pump cavity so as to pump the treatment solution between the upstream and downstream solution pumps through the bypass line, and wherein the valve arrangement is operable to selectively control the fluid communication between the bypass line and the calibration cavity.

4. The cassette of claim 3, which is associated with a controller which is coupled to the level detectors and configured to: determine, during the calibration phase, a balancing level in said pump cavity of the upstream solution pump or the downstream solution pump, such that the filling and emptying strokes have equal volumes when the balancing level replaces the lower or upper reference level in said pump cavity; and determine an adjusted stroke length for the direct gas-to-liquid interface in said pump cavity of the upstream solution pump or the downstream solution pump as a function of the level change, the balancing level, and the calibration volume, so as to achieve a given volumetric difference between the upstream and downstream solution pumps.

5. The cassette of claim 4, wherein the controller is configured to determine the adjusted stroke length by setting one of the lower and upper levels in the upstream solution pump or the downstream solution pump at a distance $\Delta h_{UF}$ from the balancing level ($h_0$), $\Delta h_{UF}=V_{UF}/V_{CAL}\cdot\Delta h$, wherein $V_{UF}$ is the given volumetric difference, $V_{CAL}$ is the calibration volume, and $\Delta h$ is the level change.

6. The cassette of claim 1, comprising a further level detector operable to indicate levels of treatment solution in the calibration cavity, wherein the valve arrangement, in the calibration phase, is operable to: selectively establish fluid communication between the bypass line and the calibration cavity during the emptying and filling strokes so as to change an initial level of treatment solution in the calibration cavity in proportion to a volumetric difference between the emptying and filling strokes, said volumetric difference being the calibration volume and being measurable by the further level detector.

7. The cassette of claim 1, wherein the valve arrangement is operable, in the calibration phase, to perform the emptying and filling strokes in synchronization, and to selectively establish the fluid communication between the bypass line and the calibration cavity only when the level detectors associated with the pump cavities indicate that the emptying stroke has reached the lower reference level or that the filling stroke has reached the upper reference level.

8. The cassette of claim 1, comprising a further level detector operable to indicate levels of treatment solution in the calibration cavity, wherein the valve arrangement, in the calibration phase, is operable to: selectively establish fluid communication between the bypass line and the calibration cavity during the emptying and filling strokes, so as to push the treatment solution into the calibration cavity to increase a level of treatment solution in the calibration cavity from an initial level to a final level, as indicated by the further level detector, and to draw the treatment solution from the calibration cavity to decrease the level of treatment solution in the calibration cavity from the final level to the initial level, wherein the calibration cavity is configured to contain the calibration volume between the initial and final levels.

9. The cassette of claim 1, wherein, in the calibration phase, the emptying stroke is performed by the upstream solution pump, and the filling stroke is performed by the downstream solution pump.

10. The cassette of claim 1, which includes an upstream subsystem for pumping the treatment solution to the dialyzer, and wherein the upstream subsystem includes the upstream solution pump.

11. The cassette of claim 10, wherein the upstream subsystem is further configured to prepare the treatment solution by mixing at least two liquid constituents, and wherein the pump cavity of the upstream solution pump has at least one inlet connected to receive the liquid constituents from the hydraulic manifold, whereby motion of the direct gas-to-liquid interface in the pump cavity causes the liquid constituents to enter via the at least one inlet and mix in the pump cavity to form the treatment solution.

12. The cassette of claim 11, wherein the liquid constituents comprise water and a concentrate.

13. The cassette of claim 12, wherein the upstream subsystem further includes a concentrate pump for providing the concentrate to the upstream solution pump, wherein the concentrate pump includes a metering cavity which is defined inside the body and connected to the hydraulic and pneumatic manifolds for defining a direct gas-to-concentrate interface in the metering cavity, wherein the valve arrangement is operable to selectively communicate the metering cavity with the pneumatic manifold so as to, during operation of the concentrate pump reciprocate the direct gas-to-concentrate interface in the metering cavity and thereby draw concentrate from the hydraulic manifold through a concentrate inlet into the metering cavity and displace the concentrate from the metering cavity through a concentrate outlet into the hydraulic manifold, wherein the concentrate outlet is arranged for fluid communication with the upstream solution pump.

14. The cassette of claim 1, wherein the valve arrangement is operable, in a gas removal phase during operation of the cassette, to seal off the pump cavity from the hydraulic manifold and selectively communicate the pump cavity with the pneumatic manifold to establish a negative pressure in the pump cavity.

15. The cassette of claim 1, wherein the body includes a plurality of solid plates of plastic material that collectively define the hydraulic manifold, the pneumatic manifold and the pump cavity of each solution pump of the set of solution pumps, the plurality of solid plates assembled to form a rectangular cuboid.

16. The cassette of claim 15, wherein the plurality of solid plates is assembled by diffusion bonding.

17. The cassette of claim 15, wherein one pair of the plurality of solid plates is configured to collectively define at least one of the hydraulic manifold and the pneumatic manifold, and wherein another pair of the plurality of solid plates is configured to collectively define all cavities.

18. The cassette of claim 15, wherein all of the cavities are defined in one of the plurality of solid plates.

19. The cassette of claim 1, wherein the body defines a plurality of valve ports on an external surface, each of the valve ports being arranged in fluid communication with either the hydraulic manifold or the pneumatic manifold, wherein the valve arrangement includes a plurality of valves that are attached to the external surface of the body in operative engagement with the valve ports, said valves being operable to selectively communicate the pump cavity of the respective solution pump with the hydraulic and pneumatic manifolds by the operative engagement with the valve ports.

20. The cassette of claim 19, wherein the hydraulic manifold includes a dedicated fluid path in the region of the valve ports, said dedicated fluid path being configured to convey at least part of heat emitted by the plurality of valves to the treatment solution before the treatment solution is provided to the dialyzer.

21. The cassette of claim 1, wherein each solution pump of the set of solution pumps is associated with an ultrasound transceiver arranged at one end of the pump cavity, and wherein the pump cavity has a reflection surface at a predetermined distance from the ultrasound transceiver, and wherein a controller is connected to the ultrasound transceiver and is operable to: identify a reference travelling time for a sound wave emitted by the ultrasound transceiver and reflected back to the ultrasound transceiver by the reflection surface; identify a current travelling time for a sound wave emitted by the ultrasound transceiver and reflected back to the ultrasound transceiver by the direct gas-to-liquid interface; and determine a location of the direct gas-to-liquid interface in the pump cavity as a function of the current travelling time, the reference travelling time and the predetermined distance.

22. The cassette of claim 1, wherein each solution pump of the set of solution pumps is associated with an ultrasound transceiver arranged at one end of the pump cavity, and wherein the pump cavity has at least two reflection surfaces at different predetermined distances from the ultrasound transceiver, and wherein a controller is connected to the ultrasound transceiver and operable to: identify a respective reference travelling time for a sound wave emitted by the ultrasound transceiver and reflected back to the ultrasound transceiver by the at least two reflection surfaces; calculate an average speed of sound in the treatment solution inside the pump cavity based on the respective reference travelling time and the different predetermined distances; identify a current travelling time for a sound wave emitted by the ultrasound transceiver and reflected back to the ultrasound transceiver by the direct gas-to-liquid interface; and determine a location of the direct gas-to-liquid interface in the pump cavity as a function of the current travelling time and the average speed of sound.

23. The cassette of claim 1, wherein each solution pump of the set of solution pumps is associated with an ultrasound transceiver arranged at one end of the pump cavity, and wherein the pump cavity has at least two reflection surfaces at different predetermined distances from the ultrasound transceiver, and wherein a controller is connected to the ultrasound transceiver and operable to: identify a respective reference travelling time for a sound wave emitted by the ultrasound transceiver and reflected back to the ultrasound transceiver by the at least two reflection surfaces; identify a current travelling time for a sound wave emitted by the ultrasound transceiver and reflected back to the ultrasound transceiver by the direct gas-to-liquid interface; and determine a location of the direct gas-to-liquid interface in the pump cavity by interpolation among the different predetermined distances based on the relation of the current travelling time to the respective reference travelling time.

24. The cassette of claim 1, wherein each solution pump of the set of solution pumps is associated with an ultrasound transceiver arranged at one end of the pump cavity, and wherein the pump cavity has a first reflection surface which is closer to the ultrasound transceiver than a nominal level in the pump cavity and a second reflection surface which is farther from the ultrasound transceiver than the nominal level.

25. The cassette of claim 1, wherein the set of solution pumps includes at least two solution pumps connected in parallel, and wherein the valve arrangement is operable to drive the direct gas-to-liquid interface in different phases in the pump cavities of the at least two solution pumps connected in parallel so as to alternately pump the treatment solution from the respective pump cavity.

26. The cassette of claim 1, wherein the first pneumatic connector is arranged for connecting the cassette to a pneumatic positive pressure source, and wherein the pneumatic manifold is further in fluid communication with a second pneumatic connector on the body for connecting the cassette to a pneumatic negative pressure source, and wherein the valve arrangement is operable to alternately communicate the pump cavity with the pneumatic positive pressure source and the negative pneumatic pressure source so as to reciprocate the direct gas-to-liquid interface in the pump cavity.

27. A dialysis machine comprising:
a cassette for pumping a treatment solution through a dialyzer in a dialysis system, said cassette including a body,
a hydraulic manifold which is defined inside the body and configured for fluid communication with a first hydraulic connector on the body, the first hydraulic connector being arranged for connecting the dialyzer to the cassette,
a pneumatic manifold which is defined inside the body and configured for fluid communication with a first pneumatic connector on the body, the first pneumatic connector being arranged for connecting the cassette to a pneumatic pressure source,
a set of solution pumps including an upstream solution pump and a downstream solution pump, each solution pump of the set of solution pumps including a pump cavity which is defined inside the body for fluid communication with the hydraulic and pneumatic manifolds,
a calibration cavity connected for fluid communication with a bypass line that extends between the upstream and downstream solution pumps, and
a valve arrangement which is operable to selectively communicate the pump cavity with the hydraulic and pneumatic manifolds so as to, during the operation of the respective solution pump, reciprocate an interface in the pump cavity and thereby displace the treatment solution through the hydraulic manifold,
wherein each of the pump cavities defines, during operation of the respective solution pump, said interface as a direct gas-to-liquid interface in the pump cavity between a gaseous substance admitted via the pneumatic manifold and the treatment solution admitted via the hydraulic manifold, and
wherein the cassette is operable in a calibration phase, in which the valve arrangement is operable to cause one of the upstream or downstream solution pumps to perform an emptying stroke that moves the direct gas-to-liquid interface from an upper reference level to a lower reference level so as to push the treatment solution into the bypass line, cause the other of the upstream or downstream solution pumps to perform a filling stroke that moves the direct gas-to-liquid interface from a lower reference level to an upper reference level so as to draw the treatment solution from the bypass line, and selectively establish fluid communication between the bypass line and the calibration cavity during the emptying and filling strokes so as to transfer a known or measurable calibration volume between the calibration cavity and the pump cavity of the upstream solution pump or the downstream solution pump, wherein a level detector is operable to measure a level change corresponding to the calibration volume in said pump cavity of the upstream solution pump or the downstream solution pump; and
a controller configured to control the operation of the valve arrangement.

28. A method of operating a cassette for pumping a treatment solution through a dialyzer in which the cassette includes (i) a body, (ii) a hydraulic manifold which is defined inside the body and configured for fluid communication with a first hydraulic connector on the body, the first hydraulic connector being arranged for connecting the dialyzer to the cassette, (iii) a pneumatic manifold which is defined inside the body and configured for fluid communication with a first pneumatic connector on the body, the first pneumatic connector arranged for connecting the cassette to a pneumatic pressure source, (iv) a set of solution pumps integrated in the cassette, each solution pump of the set of solution pumps including a pump cavity which is defined inside the body for fluid communication with the hydraulic and pneumatic manifolds, (v) a valve arrangement which is operable to selectively communicate the pump cavity with the hydraulic and pneumatic manifolds so as to, during operation of the respective solution pump, reciprocate an interface in the pump cavity and thereby displace the treatment solution through the hydraulic manifold, (vi) an upstream subsystem for providing the treatment solution to the dialyzer via the first hydraulic connector, and a downstream subsystem for pumping the treatment solution from the dialyzer via a second hydraulic connector on the body, wherein each of the pump cavities defines, during operation of the respective solution pump, said interface as a direct gas-to-liquid interface in the pump cavity between a gaseous substance admitted via the pneumatic manifold and the treatment solution admitted via the hydraulic manifold, and wherein the set of solution pumps includes an upstream solution pump in the upstream subsystem and a downstream solution pump in the downstream subsystem, and (vii) a calibration subsystem for relatively calibrating the upstream solution pump and the downstream solution pump, wherein the calibration subsystem includes a calibration cavity which is defined inside the body and connected for fluid communication with a bypass line that extends between the upstream and downstream solution pumps, wherein level detectors are associated with the upstream and downstream solution pumps to indicate levels of the treatment solution in the respective pump cavity, wherein the cassette is operable to reciprocate the direct gas-to-liquid interface between an upper level and a lower level in the respective pump cavity so as to pump the treatment solution between the upstream and downstream solution pumps through the bypass line, and wherein the valve arrangement is operable to selectively control the fluid communication between the bypass line and the calibration cavity, said method comprising:

(a) operating the valve arrangement during a calibration phase to cause, (a1) one of the upstream and downstream solution pumps to perform an emptying stroke that moves the direct gas-to-liquid interface from an upper reference level to a lower reference level so as to push the treatment solution into the bypass line, and (a2) cause the other of the upstream and downstream solution pumps to perform a filling stroke that moves the direct gas-to-liquid interface from a lower reference level to an upper reference level so as to draw the treatment solution from the bypass line, and selectively establish fluid communication between the bypass line and the calibration cavity during the emptying and filling strokes so as to transfer a known or measurable calibration volume between the calibration cavity and the pump cavity of the upstream solution pump or the downstream solution pump, wherein one of the level detectors is operable to measure a level change corresponding to the calibration volume in said pump cavity of the upstream solution pump or the downstream solution pump;

(b) determining, during the calibration phase, a balancing level ($h_0$) in said pump cavity of the upstream solution pump or the downstream solution pump, such that the filling and emptying strokes have equal volumes when the balancing level ($h_0$) replaces the lower or upper reference level in said pump cavity; and (c) determining an adjusted stroke length for the direct gas-to-liquid interface in said pump cavity of the upstream solution pump or the downstream solution pump as a function of the level change ($\Delta h$), the balancing level ($h_0$), and the calibration volume ($V_{CAL}$), so as to achieve a given volumetric difference ($V_{UF}$) between the upstream and downstream solution pumps.

* * * * *